United States Patent [19]
Hilgers

[11] Patent Number: 6,165,995
[45] Date of Patent: Dec. 26, 2000

[54] CYCLODEXTRIN-DERIVATIVES AND METHODS FOR THE PREPARATION THEREOF

[75] Inventor: Luuk Hilgers, Utrecht, Netherlands

[73] Assignee: American Cyanamid Company, Madison, N.J.

[21] Appl. No.: 08/860,454

[22] PCT Filed: Dec. 21, 1995

[86] PCT No.: PCT/BE95/00120

§ 371 Date: Sep. 15, 1997

§ 102(e) Date: Sep. 15, 1997

[87] PCT Pub. No.: WO96/20222

PCT Pub. Date: Jul. 4, 1996

[30] Foreign Application Priority Data

Dec. 27, 1994 [BE] Belgium ................................ 09401174

[51] Int. Cl.[7] ......................... A61K 31/715; A61K 39/00
[52] U.S. Cl. ......................... 514/58; 424/184.1; 514/938
[58] Field of Search ................................ 514/54, 58, 938; 424/184.1

[56] References Cited

U.S. PATENT DOCUMENTS

| | | | |
|---|---|---|---|
| 4,247,535 | 1/1981 | Lewis et al. ............................. | 514/58 |
| 5,134,127 | 7/1992 | Stella et al. ............................. | 514/58 |
| 5,180,716 | 1/1993 | Yaksh et al. ............................. | 514/58 |
| 5,385,891 | 1/1995 | Moriya et al. ............................. | 514/58 |
| 5,658,894 | 8/1997 | Weisz ..................................... | 514/58 |

FOREIGN PATENT DOCUMENTS

91/13100  9/1991  WIPO .

*Primary Examiner*—Howard C. Lee

[57] ABSTRACT

The present invention relates to cyclodextrin derivatives, and methods for the preparation thereof, which cyclodextrin derivatives have at least one but no more than N−1 "higher" alkyl groups and at least one but no more than N−1 sulfate groups, wherein the total combined number of "higher" alkyl groups and sulfate groups does not exceed N, and further wherein N is the number of hydroxyl groups of the cyclodextrin from which the derivative was derived. The "higher" alkyl groups are lipids and, more particularly, aliphatic or aromatic carbon chains, especially linear carbon chains having a general structure of —O—C(=O)—$(CH_2)_n$—$CH_3$, wherein n is between 6 and 24 and/or —OC(=O)—$(CH_2)_m$—CH=CH—$(CH_2)_m$—$CH_3$, wherein m is at least 6. The sulfate groups disclosed herein are sulfate groups having the formula —$OSO_3R$, wherein R may be H, Na, K, Li, $NH_4$ and/or other atoms/molecules that form monovalent cations. The CD derivatives are obtained in a two-step reaction wherein a cyclodextrin is contacted with acoylchloride followed by sulfonating $SO_3$-complex.

24 Claims, No Drawings

CYCLODEXTRIN-DERIVATIVES AND METHODS FOR THE PREPARATION THEREOF

The present invention relates to a novel family of cyclodextrin-derivatives and, in particular, to a novel family of cyclodextrin-derivatives having both "higher" alkyl groups and sulfate groups, which are useful for, inter alia, biopharmaceutical applications and to methods for the preparation thereof.

Cyclodextrins (CDs) are a well-known family of crystalline, nonhygroscopic molecules comprised of a chain of either six, seven or eight glucopyranose units that are joined to one another at the terminal ends thereof. Due to steric reasons, cyclodextrins form a cyclic structure of torus-shaped macrorings which have an internal axial cavity. The outer surface of these molecules is hydrophilic. The internal cavity of these molecules is of apolar nature.

Used for a variety of purposes, a particularly important use for cyclodextrins has been as a carrier for drug molecules and antigens, which may be entrapped in the internal cavity thereof.

Drawbacks with cylcodextrins include the fact that they have various physical, chemical and physiochemical properties (such as solubility) which, while being appropriate for its intended use, are not appropriate for use with other molecules and/or other uses.

To provide CDs having desired physical, chemical and physiochemical properties, various chemical and/or enzymatic modifications have been made to the CD molecule to provide CD derivatives thereof.

In such CD derivatives, at least one of the free hydroxyl groups of the CD molecule (there being three such free hydroxyl groups on each of the glucopyranose units of the CD molecule) has been modified. Such modification is made by substitution of either the hydrogen atom of the hydroxyl group or of the entire hydroxyl group itself, with one of a large variety of substituting groups. In this fashion, depending upon the number and the type of substitution(s) performed, CD derivatives may be obtained which possess certain specific physiochemical properties desired for its intended use.

Relative to the use of CD derivatives as a carrier for drug molecules and antigens, it is noted that the complexation of a drug molecule or an antigen with a CD derivative can provide significant advantages in regards to improving the bioavailability and stability of the drug molecule. In such cases, improvements in the association between the CD derivative and the drug molecule can provide concomitant improvements in the bioavailability and/or stabilization of the drug molecule.

Unfortunately, the fabrication of such CD derivatives can often prove difficult and/or involve the use of procedures which are difficult, costly and even dangerous, especially on an industrial scale.

A further problem with CD derivatives is that, like conventional CDs, they possess specific physical, chemical and physiochemical properties (such as its shape, which can effect the fitting of the guest molecule in the internal axial cavity) which, while making them suitable for specific intended purposes, limit their wider for other purposes.

Accordingly, it is obvious that there remains a need for cyclodextrin derivatives which possess physiochemical properties that permit their wider use for various purposes. It can further be seen that there remains a need for an easy, safe and inexpensive method for the preparation of such CD derivatives on an industrial scale.

It is a primary object of the present invention to provide CD derivatives which are capable of forming complexes with a wide variety of guest molecules, especially drug molecules and antigens, and which possess physiochemical properties suitable for a wide variety of purposes.

It is another primary object of the present invention to provide CD derivatives which are capable of forming complexes with particular guest molecules, and especially with particular drug molecules and antigens, and which possesses certain physiochemical properties which are suitable for the specific purpose for which it is intended.

In another aspect of the present invention, it is a primary object herein to provide simple, easy and inexpensive methods for the preparation of compositions of CD derivatives having physiochemical properties that permit their wide use for various purposes and for the preparation of CD derivatives which possess specific physiochemical properties particularly suited to particular guest molecule(s) which it is intended to carry.

In yet another aspect of the present invention, it is an object herein to use such prepared CD derivatives and compositions thereof for a wide variety of uses including, inter alia, medical purposes, such as for the preparation of vaccines and/or adjuvants for vaccines.

In accordance with the teachings of the present invention, disclosed herein are CD derivatives and compositions thereof which are capable of forming complexes with a wide variety of guest molecules, and especially with drug molecules and antigens, which are capable of stabilizing and reducing the reactivity and/or mobility of the molecule (such as a drug molecule) carried therein and which possesses physiochemical properties which are suitable for a wide variety of uses.

In further accordance with the teachings of the present invention, disclosed herein are CD derivatives and compositions thereof which are capable of forming complexes with particular guest molecules, and especially with particular drug molecules and antigens, which are capable of stabilizing and reducing the reactivity and/or mobility of the particular molecule (such as a drug molecule) carried therein and which possesses certain physiochemical properties which are suitable for the specific purpose for which it is intended.

In particular, disclosed herein are novel cyclodextrin derivatives characterized by having at least one but no more than N−1 "higher" alkyl groups and at least one but no more than N−1 sulfate groups, wherein the total combined number of "higher" alkyl groups and sulfate groups does not exceed N, and further wherein N is the total number of hydroxyl groups of the cyclodextrin from which the derivative was obtained.

As disclosed herein, N is either eighteen (when the cyclodextrin derivative is an α-CD), twenty-one (when the cyclodextrin derivative is a β-CD) or twenty-four (when the cyclodextrin derivative is an γ-CD).

If desired, the novel cyclodextrin derivatives may be further characterized by having at least one but no more than N−2 free hydroxyl groups, and wherein the total combined number of "higher" alkyl groups, sulfate groups and hydroxyl groups does not exceed N, and further wherein N is the total number of hydroxyl groups of the cyclodextrin from which the derivative was obtained.

In a particular embodiment, the novel cyclodextrin derivatives are characterized by having at least one but no more than N−7 "higher" alkyl groups and/or at least one but no more than N−7 sulfate groups.

In another particular embodiment, the novel cyclodextrin derivatives have at least one but no more than thirteen sulfate groups.

In yet another particular embodiment, the novel cyclodextrin derivatives are further characterized by the "higher" alkyl groups being lipids. In this regard, the "higher" alkyl groups may be aliphatic or aromatic carbon chains, such as linear carbon chains with the general structure being —OC(=O)—$(CH_2)_n$—$CH_3$, wherein n at least 6 and —OC(=O)—$(CH_2)_m$—CH=CH—$(CH_2)_m$—$CH_3$, wherein m is at least 6. Further disclosed are such linear carbon chains wherein n is between 6 and 24. Further disclosed are such linear carbon chains where n is between 6 and 16.

In particular, disclosed are such linear carbon chains where n may be 6 (octanoylchloride), 8 (decanoylchloride), 10 (dodecanoylchloride, —OC(=O)—$(CH_2)_{10}CH_3$, also referred to herein as lauroylchloride), 12 (tetradecanoylchloride, also known as myristoylchloride), 14 (hexadecanoylchloride, also known as palmitoylchloride) and 16 (octadecanoylchloride, such as stearoylchloride) Furthermore, disclosed herein is —OC(=O)—$(CH_2)_7$—CH=CH—$(CH_2)_7$—$CH_3$ (oleoylchloride).

In still another particular embodiment, the novel cyclodextrin derivatives are further characterized by the sulfate groups having the general formula —$OSO_3R$, wherein R is selected from the group consisting of atoms and/or molecules that form monovalent cations. Examples of members of such a group include H, Na, K, Li and $NH_4$. Specific embodiments include cyclodextrin derivatives characterized by the sulfate groups —$OSO_3H$ and —$OSO_3Na$.

In another aspect of the teachings of the present invention, disclosed herein are easy, safe and inexpensive methods for the preparation of CD derivatives, including the CD derivatives of the present invention.

In particular, disclosed herein are methods for preparing compositions of CD derivatives having physiochemical properties which are suitable for use with a wide variety of guest molecules with which it may be associated, as well as methods for preparing CD derivatives and compositions thereof which possess specific physiochemical properties particularly suited to the guest molecule which it is intended to carry.

In this regard, disclosed herein is a process for the preparation of the cyclodextrin derivatives and compositions thereof, characterized by the steps of contacting a cyclodextrin with both acoylchloride(s) and sulfonating $SO_3$-complex(es).

Preferred acoylchlorides are octanoylchloride, decanoylchloride, dodecanoylchloride (lauroylchloride), tetradecanoylchloride (myristoylchloride), hexadecanoylchloride (palmitoylchloride) and octadecanoylchloride (stearoylchloride and oleoylchloride).

Preferred sulfonating $SO_3$-complexes are $HClSO_3$ (chlorosulphonic acid), $SO_3$-pyridine, $SO_3$-2-methylpyridine, $SO_3$-2,6-dimethylpyridine, $SO_3$-dimethylformamide, $SO_3$-trimethylamine, $SO_3$-triethylamine, $SO_3$-dimethylanaline, $SO_3$-N-ethylmorpholine, $SO_3$-diethylanaline and $SO_3$-dioxane.

Preferably, the cyclodextrin is contacted with the acoylchloride(s), whereby an L-CD derivative is formed, prior to contacting with the sulfonating $SO_3$-complex(es).

The method is further characterized in that approximately 1 mole of cyclodextrin is contacted with at least about 1 mole but no more than about N−1 moles of the acoylchloride(s) and with at least about 1 mole but no more than about N−1 moles of the sulfonating $SO_3$ -complex(es), wherein the total combined number of moles of acoylchloride and sulfonating $SO_3$-complex does not exceed N, and wherein N is the total number of hydroxyl groups of the cyclodextrin contacted.

Preferably, such contact is carried out in the presence of organic solvent(s).

In a preferred embodiment, the cyclodextrin is contacted with the acoylchloride(s) for about 6 hours at approximately 60° C.

In another preferred embodiment, the cyclodextrin is contacted with the sulfonating $SO_3$-complex(es) for at least one hour at room temperature.

In a further embodiment, the method is further characterized by removing the organic solvent(s) from the CD derivatives so obtained. In this respect, it is preferred that such a removal of organic solvent(s) from the CD derivatives includes dialyzing or ultrafiltrating the CD derivatives so obtained.

In a still further embodiment, the method is further characterized by dialyzing or ultrafiltering the CD derivatives in the presence of a nondialyzable detergent, whereby the CD derivatives are separated or removed from the organic solvent(s) used for the preparation (synthesis) thereof.

In a still further embodiment, the method is further characterized by lyophilizing the CD derivatives separated or removed from organic solvent(s), whereby a dry CD derivative product is obtained.

In another aspect of the present invention, disclosed herein are methods for preparing compositions rich in CD derivatives having specific numbers and types of sulfate and "higher" alkyl groups, so as to be capable of forming complexes with particular guest molecules, and especially with particular drug molecules and antigens, which are capable of stabilizing and reducing the reactivity and/or mobility of the particular molecule (such as a drug molecule) carried therein and which possesses certain physiochemical properties which are suitable for the specific purpose for which it is intended.

In particular, disclosed herein are methods for preparing compositions rich in CD derivatives having a particular number of sulfate groups and "higher" alkyl groups per CD derivative, characterized by the steps of contacting approximately 1 mole of cyclodextrin with about 1 mole of acoylchloride(s) for each "higher" alkyl group desired per CD derivative prepared thereby and with about 1 mole of sulfonating SO3-complex(es) for each sulfate group desired per CD derivative prepared thereby, wherein the total combined number of moles of acoylchloride(s) and the sulfonating $SO_3$-complex(es) does not exceed N, and wherein N is the total number of hydroxyl groups of the cyclodextrin contacted.

In this fashion, compositions rich in CD derivatives having specific numbers of sulfate groups and "higher" alkyl groups per molecule of CD derivative are formed having physiochemical properties particularly suited for use with specific guest molecule(s) with which it is intended to be associated.

In one embodiment, disclosed herein are methods for preparing CD derivatives having higher water solubility, lower solubility in apolar solvents and a decreased capacity to bind to hydrophobic surfaces. In this respect, it is preferred that the acoylchloride(s) are octanoylchloride, decanoylchloride, dodecanoylchloride (lauroylchloride) and/or tetradecanoylchloride (myristoylchloride). More preferably in this regard, the acoylchloride(s) are octanoylchloride, decanoylchloride and/or dodecanoylchloride (lauroylchloride). Most preferably in this regard, the acoylchloride(s) are octanoylchloride and/or decanoylchloride.

In a still yet further embodiment, disclosed herein are methods for preparing CD derivatives having lower water solubility, higher solubility in apolar solvents and an increased capacity to bind to hydrophobic surfaces. In this respect, it is preferred that the acoylchloride(s) are dodecanoylchloride (lauroylchloride), tetradecanoylchloride (myristoylchloride), hexadecanoylchloride (palmitoylchloride) and/or octadecanoylchloride (stearoylchloride and oleoylchloride). More preferably in this regard, the acoylchloride(s) are tetradecanoylchloride (myristoylchloride), hexadecanoylchloride (palmitoylchloride) and/or octadecanoylchloride (stearoylchloride and oleoylchloride). Most preferably in this regard, the acoylchloride(s) are hexadecanoylchloride (palmitoylchloride) and/or octadecanoylchloride (stearoylchloride and oleoylchloride).

In a further embodiment, the method is further characterized by dialyzing or ultrafiltrating the CD derivatives so obtained in the presence of a monovalent cations being $H^+$, $K^+$, $Li^+$, $Na^+$ and/or $NH_4^+$, whereby CD derivatives having sulfate groups including the atoms/molecules of said cations are provided.

In a yet further embodiment, the dialyzing or ultrafiltrating the CD derivatives so obtained is done in the presence of $H^+$ and/or $NH_4^+$, whereby CD derivatives having higher water solubility and a higher solubility in apolar solvents are provided.

In a still yet further embodiment, the dialyzing or ultrafiltrating the CD derivatives so obtained is done in the presence of $K^+$ and/or $Na^+$, whereby CD derivatives having lower water solubility, lower solubility in apolar solvents are provided.

In still another aspect of the present invention, disclosed herein are uses for such prepared CD derivatives including, inter alia, uses for medical purposes.

In this regard, disclosed herein is a therapeutic composition having a CD derivative having at least one but no more than N−1 "higher" alkyl groups and at least one but no more than N−1 sulfate groups, and wherein the total combined number of "higher" alkyl groups and sulfate groups does not exceed N, and further wherein N is the total number of hydroxyl groups of the cyclodextrin from which the derivative was obtained.

Particularly disclosed herein are adjuvants for use with various vaccines, which adjuvants are characterized by having a CD derivative in an oil-in-water emulsion, the CD derivative having at least one but no more than N−1 "higher" alkyl groups and at least one but no more than N−1 sulfate groups, and wherein the total combined number of "higher" alkyl groups and sulfate groups does not exceed N, and further wherein N is the total number of hydroxyl groups of the cyclodextrin from which the derivative was obtained.

The nature and the substance of the teachings of the present invention, as well as objects and advantages thereof, will become more fully appreciated and better understood by reference to the following description when read in conjunction with the accompanying figures.

The present invention relates to our finding of a family of CD derivatives having "higher" alkyl groups and sulfate groups, and compositions thereof which have desired physiochemical properties.

The present invention further relates to our finding of a simple and easy method for safely preparing a family of CD derivatives wherein various (or all) of the hydroxyl groups (and/or portions thereof) of the CD molecule are substituted with "higher" alkyl groups and with sulfate groups, so as to provide CD derivatives having physiochemical properties that are suitable for a wide variety of uses.

Further, and as will be discussed at length below, we have found that, in using the method of the present, by either: (1) varying the quantity (ratios) of the various starting materials used; and/or (2) varying the acoylchloride(s) used; and/or (3) varying the cation(s) employed in the aqueous solution used for dialysis or ultrafiltration in practicing the method of the present invention, different compositions of CD derivatives may be produced having higher or lower quantities of (are rich in) certain CD derivatives having specific physiochemical properties which are particularly suitable for use with particular molecule(s) and/or particular use(s).

As used herein, the term "higher alkyl groups" refers to linear hydrocarbon chains of at least eight carbon atoms.

As used herein, the term "sulfate groups" refers to groups having the general formula $-OSO_3R$, wherein R is selected from the group consisting of atoms and/or molecules that form monovalent cations. Examples of members of such a group are H, Na, K, Li and $NH_4$.

As used herein, the term "hydroxyl groups" refers to groups having the formula $-OH$.

The method of the present invention is usable with cyclodextrins which are comprised of either six glucopyranose units ($\alpha$-cyclodextrins), seven glucopyranose units ($\beta$-cyclodextrins) and/or eight glucopyranose units ($\gamma$-cyclodextrins) for producing cyclodextrin derivatives which contain the same number of glucopyranose units.

The method of the present invention for preparing the CD derivatives of the present invention is a simple, easy and safe to perform two-step reaction, comprised of: (1) first, contacting a cyclodextrin with one or more acoylchloride to form lipidic CD (L-CD) derivatives; and (2) second, contacting the formed lipidic CD derivatives with one or more sulfonating $SO_3$-complex to form the sulfo-lipidic CD (SL-CD) derivatives of the present invention.

The two steps involved in the synthesis of the CD derivatives of the present invention are considered to be ad random reactions, resulting in a collection of different CD derivatives which vary in sulphate groups and "higher" alkyl groups content and, consequently, in the structure and physiochemical properties possessed thereby.

In the first step of this process, approximately 1 mole of cyclodextrin is contacted with at least about 1 mole but no more than about N−1 moles of acoylchloride(s), wherein the total combined number of moles of acoylchloride(s) and sulfonating $SO_3$-complex(es) does not exceed N, and wherein N is the total number of hydroxyl groups of the cyclodextrin contacted.

In this step, the cyclodextrin is contacted with the acoylchloride(s) for about 6 hours at approximately 60° C. If desired, the cyclodextrin can be further contacted with the acoylchloride(s) for approximately 18 additional hours at room temperature.

In the second step of this process, approximately 1 mole of cyclodextrin is contacted with from approximately 1 mole to approximately N−1 mole of sulfonating $SO_3$-complex (es), wherein the total combined number of moles of acoylchloride(s) and sulfonating $SO_3$-complex(es) does not exceed N, and wherein N is the total number of hydroxyl groups of the cyclodextrin contacted.

In this step, the cyclodextrin is contacted with the sulfonating $SO_3$-complex(es) for at least one hour at room temperature. If desired, such contact can be for as long as (or longer than) 24 hours.

Relative to the above, it is noted that performance of the process at room temperature means that the temperature is not critical to the process. Such a feature permits the process to be performed at a wide range of temperatures and under a wide range of conditions with concommittant savings.

In this regard, it is contemplated herein that room temperatures no lower than about 10° C. would be acceptable.

Preferred would be temperatures no lower than about 15° C. More preferred would be temperatures no lower than about 18° C. Most preferred would be temperatures no lower than about 22° C.

Further in this regard, room temperatures no higher than about 50° C. would be acceptable. Preferred would be temperatures no higher than about 40° C. More preferred would be temperatures no higher than about 25° C. Most preferred would be temperatures no higher than about 22° C.

The two steps of the present invention are carried out in the presence of organic solvent(s) in which the cyclodextrin from which the derivatives are made are solubilized. Preferred in this regard is a mixture of anhydrous dimethylformamide and anhydrous pyridin and/or a mixture of anhydrous N-methylpyrrolidinone and anhydrous pyridin.

The CD derivative(s) which is (are) produced by the use of the method of the present invention are removed from the organic solvents. It is preferred that such a removal of solvents from the CD derivatives includes dialyzing or ultrafiltering the CD derivatives so obtained. In this respect, it is noted that in such processes, monovalent cations may be employed. These monovalent cations are, preferably, $K^+$, $Li^+$, $H^+$, $Na^+$, and $NH_4^+$.

It is further noted that such dialyzing or ultrafiltering may be done in the presence of a nondialyzable detergent, thereby transferring the CD derivatives from the organic solvents used for synthesis to aqueous solutions for their further use. Examples of such nondialyzable detergents are TWEEN 80 and TRITON X-100.

The CD products from which solvent has been removed may then be lyophilized if a dry CD derivative product is desired. In doing so, any lyophilization procedure, well-known to those skilled in the art, which is useful for obtaining dry products from aqueous solutions may be employed. In this respect, we note that, preferably, such lyophilization be performed at room temperature, at an internal pressure of less than 0.1 mbar and a cold trap of less than −25° C.

As noted above, in practicing the method of the present invention, the production of certains of the CD derivatives may be increased and/or decreased, as desired, by : (1) varying the quantities (ratios) of the starting materials; and/or (2) varying the types of the starting materials; and/or (3) varying the types of cation(s) in the aqueous solution used for dialysis or ultrafiltration.

Varying the quantity (ratios) of the starting materials by increasing the quantity of sulfonating SO3-complex(es) and/or by decreasing the quantity of acoylchloride(s) employed in the process of the present invention, CD derivatives having more sulfate groups relative to "higher" alkyl groups may be provided. Conversely, by decreasing the quantity of sulfonating $SO_3$-complex(es) and/or by increasing the quantity of acoylchloride(s) employed in the process of the present invention, CD derivatives having more "higher" alkyl groups relative to sulfate groups may be provided.

For illustration of this point, using five moles of sulfonating $SO_3$-complex (such as chlorosulphonic acid) and 3 moles of acoylchloride (such as lauroylchloride) will provide a composition which is rich in CD derivatives having 5 sulfate groups and 3 "higher" alkyl groups. Similarily, using 5 moles of sulfonating $SO_3$-complex (such as chlorosulphonic acid) and 11 moles acoylchloride (such as lauroylchloride) will provide a composition rich in CD derivatives having 5 sulfate groups and 11 "higher" alkyl groups.

Varying the acoylchloride(s) employed in the process of the present invention, provides CD derivatives having different "higher" alkyl groups possessing specific desired physiochemical properties which are particularly suitable for use with particular molecule(s) and/or particular use(s). For example, octanoylchloride will yield alkyl groups of the formula $—OC(=O)—(CH_2)_6—CH_3$, decanoylchloride will yield alkyl groups of the formula $—OC(=O)—(CH_2)_8—CH_3$, dodecanoylchloride will yield alkyl groups having the formula $—OC(=O)—(CH_2)_{10}CH_3$, tetradecanoylchloride will yield alkyl groups having the formula $—OC(=O)—(CH_2)_{12}—CH_3$, hexadecanoylchloride will yield alkyl groups having the formula $—OC(=O)—(CH_2)_{14}—CH_3$ and octadecanoylchloride will yield alkyl groups having the formula $—OC(=O)—(CH_2)_{16}—CH_3$ or $—OC(=O)—(CH_2)_7—CH=CH—(CH_2)_7—CH_3$.

Varying the type of cation(s) employed in the aqueous solution used for dialysis or ultrafiltration in the process of the present invention by using $H^+$, $K^+$, $Na^+$, $NH_4^+$ and/or $Li^+$, provides CD derivatives having different sulfate groups ($—OSO_3H$, $—OSO_3K$, $—OSO_3Na$, $—OSO_3NH_4$ and $—OSO_3Li$, respectively)—possessing specific desired physiochemical properties which are particularly suitable for use with particular molecule(s) and/or particular use(s).

In the above fashion, the production of certain CD derivatives may be increased/decreased as desired, so that the composition obtained thereby contains higher or lower quantities of (is rich in) certain CD derivatives having specific physiochemical properties which are particularly suitable for use with particular molecule(s) and/or particular use(s).

This is based upon our finding, which will be discussed at length below, that the physiochemical properties of the CD derivatives prepared according to the method of the present invention depends on the ratio of the sulfate groups, "higher" alkyl groups and hydroxyl groups present, the type of counter-ion of the sulphate groups, and the type of "higher" alkyl groups of the CD derivative. The hydrophobic character of the "higher" alkyl group is of particular note in this regard.

Physiochemical properties of the CD derivatives of the present invention which may be so adjusted include, among others, solubility in aqueous (water) and nonaqueous (apolar) solvents, the capacity to form micelles and mixed micelles with other compounds, the capacity to adsorb to hydrophobic surfaces and surface-activity/tenso-activity.

The production of compositions rich in CD derivatives of higher (or increased) water solubility may be increased by:

(1) increasing the quantity of sulfonating $SO_3$-complex (es) employed in the method of the present invention and/or by decreasing the quantity of acoylchloride(s) employed in the method of the present invention, so that CD derivatives having greater numbers of sulfate groups are provided relative to the number of "higher" alkyl groups present; and/or (2) employing octanoylchloride, decanoylchloride, dodecanoylchloride (lauroylchloride) and/or tetradecanoylchloride (myristoylchloride) as the acoylchloride reagent(s); and/or (3) selecting $H^+$ and/or $NH_4^+$ as the counter-ion for the sulfate groups in either dialysis and/or ultrafiltration, which provides the CD derivative produced thereby with the sulfate groups $—OSO_3H$ and $—OSO_3NH_4$, respectively.

Conversely, the production of compositions rich in CD derivatives of lower (or decreased) water solubility may be increased by:

(1) decreasing the quantity of sulfonating $SO_3$-complex (es) employed in the method of the present invention and/or by increasing the quantity of acoylchloride(s) employed in the method of the present invention, so that CD derivatives having lower numbers of sulfate groups are provided relative to the number of "higher" alkyl groups present; and/or (2) employing dodecanoylchloride (lauroylchloride), tetradecanoylchloride (myristoylchloride), hexadecanoylchloride (palmitoylchloride) and/or octadecanoylchloride (stearoylchloride and oleoylchloride), as the acoylchloride reagent(s); and/or (3) selecting $K^+$ and/or $Na^+$ as the counter-ion for the sulfate groups in either dialysis and/or ultrafiltration, which provides the CD derivative produced thereby with the sulfate groups —$OSO_3K$ and —$OSO_3Na$, respectively.

The production of compositions rich in CD derivatives of higher (or increased) solubility in apolar solvents (such as chloroform, methyl tert-butyl ether, dichloromethane, hexadecane and mineral oil) may be increased by:

(1) decreasing the quantity of sulfonating $SO_3$-complex (es) employed in the method of the present invention and/or by increasing the quantity of acoylchloride(s) employed in the method of the present invention; and/or (2) employing dodecanoylchloride (lauroylchloride), tetradecanoylchloride (myristoylchloride) hexadecanoylchloride (palmitoylchloride) and/or octadecanoylchloride (stearoylchloride and oleoylchloride), as the acoylchloride reagent(s); and/or (3) selecting $H^+$ and/or $NH_4^+$ as the counter-ion for the sulfate groups in either dialysis and/or ultrafiltration, which provides the CD derivative produced thereby the with sulfate groups —$OSO_3H$ and —$OSO_3NH_4$, respectively.

Conversely, the production of compositions rich in CD derivative which have lower (or decreased) solubility in apolar solvents may be provided by:

(1) increasing the quantity of sulfonating $SO_3$-complex (es) employed in the method of the present invention and/or by decreasing the quantity of acoylchloride(s) employed in the method of the present invention; and/or (2) employing octanoylchloride, decanoylchloride, dodecanoylchloride (lauroylchloride) and/or tetradecanoylchloride (myristoylchloride), as the acoylchloride reagent(s); and/or (3) employing $K^+$ and/or $Na^+$ as the counter-ion for the sulfate groups in either dialysis and/or ultrafiltration, which provides the CD derivative produced thereby with the sulfate groups —$OSO_3K$ and —$OSO_3Na$, respectively.

The production of compositions rich in CD derivatives which have a higher (or increased) capacity to form micelles may be provided by increasing the quantity of sulfonating $SO_3$-complex(es) employed in the method of the present invention and by increasing the quantity of acoylchloride(s).

Conversely, the production of compositions which are rich in CD derivatives which have a lower (or decreased) capacity to form micelles may be provided by decreasing the quantity of sulfonating $SO_3$-complex(es) employed in the method of the present invention and by decreasing the quantity of acoylchloride(s).

The production of compositions which are rich in CD derivatives having a higher (or increased) surface activity/tensio-activity may be provided by increasing the quantity of both the sulfonating $SO_3$-complex(es) used and the quantity of acoylchloride(s) employed in the process of the present invention.

Conversely, the production of compositions which are rich in CD derivatives having a lower (or decreased) surface activity/tensio-activity may be provided by decreasing the quantity of both the sulfonating $SO_3$-complex(es) employed and the quantity of acoylchloride(s) employed in the process of the present invention.

The production of compositions rich in CD derivatives which have a higher (or increased) capacity to bind to hydrophobic surfaces may be provided by employing dodecanoylchloride (lauroylchloride), tetradecanoylchloride (myristoylchloride), hexadecanoylchloride (palmitoylchloride) and/or octadecanoylchloride (stearoylchloride and oleoylchloride) as the acoylchloride reagent(s).

Conversely, the production of compositions rich in CD derivatives which have a lower (or decreased) capacity to bind to hydrophobic surfaces may be provided by employing octanoylchloride, decanoylchloride, dodecanoylchloride (lauroylchloride) and/or tetradecanoylchloride (myristoylchloride) as the acoylchloride reagent(s).

By using the methods of the present invention, compositions of novel cyclodextrin derivatives may be provided.

The novel cyclodextrin derivatives provided by the process of the present invention may be cyclodextrins derivatives which are comprised of either six glucopyranose units ($\alpha$-cyclodextrins), seven glucopyranose units ($\beta$-cyclodextrins) or eight glucopyranose units ($\gamma$-cyclodextrins).

The physicochemical properties of the CD derivatives of the present invention depends on the number (and ratio) of sulfate groups and (to) "higher" alkyl groups (and to a lesser extent the number of hydroxyl groups) which are present as well as the nature of the counter-ion of the sulfate groups and the type and nature of the "higher" alkyl groups.

The novel cyclodextrin derivatives of this composition have both sulfate groups and "higher" alkyl groups (and, if desired, hydroxyl groups) that are covalently-linked to the CD molecule. In particular, in the novel cyclodextrin derivatives of the present invention, such groups are substituted for various of the free hydroxyl groups which are present on the conventional CD molecule from which the derivative was obtained. Such compositions of CD derivatives have physiochemical properties which are suitable for a wide variety of uses.

In the CD derivatives produced according to the methods of the present invention, the "higher" alkyl groups are lipid groups. In this regard, preferred lipid groups are aliphatic or aromatic carbon chains, such as linear carbon chains with the general structure being —$OC(=O)$—$(CH_2)_n$—$CH_3$, wherein n at least 6 and —$OC(=O)$—$(CH_2)_m$—$CH=CH$—$(CH_2)_m$—$CH_3$, wherein m is at least 6. Preferred are such linear carbon chains wherein n is between 6 and 24. Further preferred are such linear carbon chains where n is between 6 and 16.

In particular, "higher" alkyl groups may be linear carbon chains where n is 6 (octanoylchloride), 8 (decanoylchloride), 10 (dodecanoylchloride, —$OC(=O)$—$(CH_2)_{10}CH_3$, also referred to herein as lauroylchloride), 12 (tetradecanoylchloride, also known as myristoylchloride), 14 (hexadecanoylchloride, also known as palmitoylchloride) and 16 (octadecanoylchloride, such as stearoylchloride) Furthermore, disclosed herein is —$OC(=O)$—$(CH_2)_7$—$CH=CH$—$(CH_2)_7$—$CH_3$ (oleoylchloride).

In the CD derivatives produced according to the methods of the present invention, the sulfate groups are hydrophilic groups. Preferred sulfate groups are those having the general formula —$OSO_3R$, wherein R is selected from (the group consisting of) atoms and/or molecules that form monovalent cations. Examples of such atoms/molecules are H, Na, K, Li and $NH_4$. Particularily preferred sulfate groups are —$OSO_3H$ and —$OSO_3Na$.

If desired, the novel cyclodextrin derivatives may further have free hydroxyl groups having the formula —OH. However, we note that, if desired, the CD derivatives disclosed herein may have no hydroxyl groups.

The novel cyclodextrin derivatives of the present invention have at least one but no more than N–1 of the "higher" alkyl groups and at least one but no more than N–1 of the sulfate groups, wherein the total combined number of "higher" alkyl groups and sulfate groups does not exceed N, and further wherein N is the total number of hydroxyl groups of the cyclodextrin from which the derivative was obtained.

In particular, the CD derivatives disclosed herein may have at least one but no more than N–1 of such "higher" alkyl groups, wherein N is the total number of hydroxyl groups of the cyclodextrin from which the derivative was obtained. Further CD derivatives disclosed herein have no more than N–7 such "higher" alkyl groups, wherein N is the total number of hydroxyl groups of the cyclodextrin from which the derivative was obtained.

The CD derivatives disclosed herein at least one, but no more than N–1 of such sulfate groups, wherein N is the total number of hydroxyl groups of the cyclodextrin from which the derivative was obtained. Further CD derivatives disclosed herein have no more than N–7 such sulfate groups, wherein N is the total number of hydroxyl groups of the cyclodextrin from which the derivative was obtained. Still further CD derivatives disclosed herein have no more than seven such sulfate groups.

In any event, the total combined number of sulfate and "higher" alkyl groups will be between 2 and N, wherein N is the total number of hydroxyl groups of the cyclodextrin from which the derivative was obtained. Further, CD derivatives of the present invention have a combined total of sulfate and "higher" alkyl groups of between 4 and N–7, wherein N is the total number of hydroxyl groups of the cyclodextrin from which the derivative was obtained.

Generally, the novel cyclodextrin derivatives are further characterized by having at least one but no more than thirteen sulfate groups.

Should the CD derivatives disclosed herein have hydroxyl groups, at least one but no more than N–2 such hydroxyl groups may be present, wherein N is the total number of hydroxyl groups of the cyclodextrin from which the derivative was obtained. Further CD derivatives disclosed herein have no more than N–4 such hydroxyl groups, wherein N is the total number of hydroxyl groups of the cyclodextrin from which the derivative was obtained.

In such an event, the combined total of sulfate groups, "higher" alkyl groups and hydroxyl groups will not exceed N, wherein N is the total number of hydroxyl groups of the cyclodextrin from which the derivative was obtained.

In the above regard, if the cyclodextrin from which the derivative was obtained has six glucopyranose units, N will be eighteen, if the cyclodextrin from which the derivative was obtained has seven glucopyranose units, N will be twenty-one, and if the cyclodextrin from which the derivative was obtained has eight glucopyranose units, N will be twenty-four.

In another aspect of the present invention, CD derivatives are provided having ratios of sulfate groups to "higher" alkyl groups which provide the CD derivative with physiochemical properties that are specifically suited (optimized) for a particular intended purpose or use.

In this regard, many different CD derivatives of the present invention have been synthesized according to the methods of the present invention, to provide CD derivatives which have specific physiochemical properties. Depending upon the profile of the pharmaceutical form and physiochemical and biological properties of the drug molecule complexed therewith and carried thereby, different CD derivatives demonstrate distinct efficacy with potential advantages in certain cases.

CD derivatives are provided herein having physiochemical properties such as, among others, solubility in aqueous and nonaqueous solvents, the capacity to form micelles, the capacity to form mixed micelles with other compounds, the capacity to adsorb to hydrophobic surfaces and specific surface-activity/tenso-activity.

In particular, CD derivatives having increased water solubility are provided wherein the ratio of sulfate groups present to "higher" alkyl groups present is increased. This can also be achieved by, for example, the sulfate groups being —$OSO_3H$ and —$OSO_3NH_4$ and/or the "higher" alkyl groups being —$OC(=O)$—$(CH_2)_nCH_3$, wherein n is 6–12, as was discussed at length above.

Conversely, CD derivatives having decreased water solubility are provided as the ratio of sulfate groups present to "higher" alkyl groups present is decreased. This can also be achieved by, for example, the sulfate groups being —$OSO_3K$ and —$OSO_3Na$ and/or the "higher" alkyl groups being —$OC(=O)$—$(CH_2)_nCH_3$, wherein n is 12–18 and/or —$OC(=O)$—$(CH_2)_m$—$CH=CH$—$(CH_2)_m$—$CH_3$, wherein m is at least 6, as was discussed at length above.

To illustrate the point involving ratios, the following examples are cited CD derivatives which have 2 sulfate groups and 10 "higher" alkyl groups are more water soluble than CD derivatives having 2 sulfate groups and 11 or more "higher" alkyl groups, but are less water soluble than CD derivatives having 2 sulfate groups and 9 or less "higher" alkyl gropus. Similarily, CD derivatives having 2 sulfate groups and 10 "higher" alkyl groups will be more water soluble than CD derivatives having 1 sulfate group and 10 "higher" alkyl groups but less water soluble than CD derivatives having 3 sulfate groups and 10 "higher" alkyl groups.

CD derivatives having increased solubility in apolar solvents (such as chloroform, methyl tert-butyl ether, dichloromethane, hexadecane and mineral oil) are provided as the ratio of sulfate groups present to "higher" alkyl groups present is increased. This can also be achieved by, for example, the sulfate groups being —$OSO_3H$ and —$OSO_3NH_4$ and/or the "higher" alkyl groups being —$OC(=O)$—$(CH_2)_nCH_3$, wherein n is 12–18 and/or —$OC(=O)$—$(CH_2)_m$—$CH=CH$—$(CH_2)_m$—$CH_3$, wherein m is at least 6, as was discussed at length above.

Conversely, CD derivatives having a decreased solubility in apolar solvents are provided as the ratio of sulfate groups present to "higher" alkyl groups present is increased. This can also be achieved by, for example, the sulfate groups being —$OSO_3K$ and —$OSO_3Na$ and/or the "higher" alkyl groups being —$OC(=O)$—$(CH_2)_nCH_3$, wherein n is 6–12, as was discussed at length above.

CD derivatives having an increased capacity to form micelles are provided as the the number of sulfate groups present and the number of hydrophobic (i.e., "higher" alkyl) groups present is increased.

Conversely, CD derivatives having a decreased capacity to form micelles are provided as the number sulfate groups present and the number of hydrophobic (i.e., "higher" alkyl) groups present is decreased.

In the above regard, the CD derivatives of the present invention can form large mixed micelles with other compounds. For example, a CD derivative with a sulfate/lauroyl ratio of 1.4 sulfate groups to 7.7 lauroyl groups per CD dervative molecule forms large mixed micelles with TWEEN 80 (MERCK) which do not pass ultrafiltration membranes with a cut-off as high as 100,000 daltons. The size of the mixed micelles with other compounds depends on the ratio of the hydrophilic (i.e., sulfate) groups and hydrophobic (i.e., "higher" alkyl) groups, on the hydrophobicity of the hydrophobic groups and on the physiochemical features of the molecule to be associated therewith.

CD derivatives having an increased surface activity/tensio-activity are provided as the total number of sulfate groups present is increased and/or the total number of hydrophobic (i.e., "higher" alkyl) groups present is increased and/or as the total number of sulfate groups present and "higher" alkyl groups present is increased.

CD derivatives having a decreased surface activity/tensio-activity are provided as the total number of sulfate groups is decreased and/or the total number of hydrophobic (i.e., "higher" alkyl) groups present is decreased and/or as the total number of sulfate groups present and "higher" alkyl groups present is decreased.

In illustration of the above, CD derivatives of the present invention can bind to hydrophobic surfaces (for example, the CD derivatives of the present invention with a ratio (per CD derivative) of sulfate groups to lauroyl groups of 1.4 sulfate groups to 7.7 lauroyl groups per CD derivative molecule binds to droplets of a squalane-in-water emulsion.

CD derivatives having an increased capacity to bind to hydrophobic surfaces are provided by the "higher" alkyl groups being provided by the "higher" alkyl groups being —OC(=O)—(CH$_2$)$_n$CH$_3$, wherein n is 12–18 and/or —OC(=O)—(CH$_2$)$_m$—CH=CH—(CH$_2$)$_m$—CH$_3$, wherein m is at least 6, as was discussed at length above.

Conversely, CD derivatives having a decreased capacity to bind to hydrophobic surfaces are provided the "higher" alkyl groups being —OC(=O)—(CH$_2$)$_n$CH$_3$, wherein n is 6–12, as was discussed at length above.

By using the methods of the present invention, compositions of novel cyclodextrin derivatives may be provided which may be used as such, without being separated from the other CD derivatives which are produced and which are present therewith.

However, if desired and/or necessary, certain(s) of the CD derivative(s) which is (are) produced by the use of the method of the present invention may then be separated and purified from the remainder of the CD derivatives produced for subsequent use thereof, by the use of classical methods well-known in the art, such as ion-exchange chromatography, reverse-phase chromatography, crystallization from solutions, etc.

The CD derivatives disclosed herein, when complexed with a molecule (such as a drug molecule or antigen), provides improved bioavailability of the molecule from solid and/or semisolid and/or liquid formulations. They also provide enhanced stability and improved shelf-life. Further, they reduced the side effects (toxicity) of the guest molecule carried thereby. Finally, they make possible the provision of uniform easy-to-handle powders (even from liquids) and aqueous injectable solutions (from poorly-soluble drugs).

The novel CD derivatives of the present invention may be used for those same purposes which CDs and other CD derivatives are presently and conventionally employed. In particular, it is contemplated herein that the CD derivatives of the present invention may be used for medical purposes as a carrier for drug molecules and antigens.

In this regard, the CD derivatives of the present invention may, using protocols and under conditions which are well-known to those skilled in the art, be complexed with drug molecules and/or antigens (which are also well-known to those skilled in the art for medical uses) to produce therapeutic and/or prophylactic compositions, such as vaccines and other therapeutic and/or prophylatic compositions, which may then be used as such for medical purposes.

An example of such a medical use is the use of the CD derivatives (and compositions thereof) in adjuvants. Suitable adjuvants include those commonly referred to as oil-in-water (including squalane-in-water, mineral oil-in-water and soya oil-in-water) emulsions.

Having described the preferred embodiments of the CD derivatives of the present invention and the methods for the production thereof, reference is now made to the following examples which are meant herein to be illustrative only.

EXAMPLE 1

For the synthesis of the cyclodextrins of the present invention, as described in this and the following examples, the utmost precautions were taken to avoid contacting the different starting materials with water.

Water was removed from 4 gram samples of β-CD (ACROS) by heating of the 4 gram samples for 4 hours at 120° C.

Water was removed from a 1:1 (v/v) mixture of anhydrous dimethylformamide (JANSSEN CHEMICA) and anhydrous pyridin (JANSSEN CHEMICA) by adding thereto molecular sieves (2A by MERCK, Darmstadt Germany) and incubating the mixture in a closed container for at least 48 hours at room temperature. The anhydrous dimethylformamide/pyridin mixture was then separated from the molecular sieves by decanting the anhydrous mixture into a dry container.

Respective 4 gram samples of the dried CD was then solubilized in respective 50 ml samples of the anhydrous dimethylformamide/pyridin mixture.

Lauroylchloride (MERCK, GERMANY) was then added to the respective solubilized CD samples in the quantities set forth below in Table 1 and the reaction mixtures incubated for six hours at 60° C., followed by incubation for 18 hours at temperatures of between 15 and 22° C. (room temperature). In this manner, L-CD solutions were obtained.

Chlorosulphonic acid (MERCK, GERMANY), in the quantities set forth below in Table 1, were added to respective samples of the anhydrous dimethylformamide/pyridin mixture which was prepared as described above. These respective mixtures were then added to respective L-CD solutions, as is also set forth in Table 1. The reaction mixtures thus obtained were then incubated for 24 hours at a temperature of between 15 and 22° C. (room temperature).

Following incubation, solvents were then partially removed from the reaction mixtures by evaporation at low pressure (200 millibars) for 1–2 hours at 60° C. Solvents were further removed by extensive dialysis using a membrane of regenerated cellulose with a cut-off of between 1,000 and 10,000 daltons (SPECTRA/POR) against isotonic phosphate buffered saline (PBS comprised of, per liter of water: 8 g sodium chloride, 0.2 g potassium chloride and 1.15 g disodium hydrogen phosphate having a pH of 7.3) and subsequently against ultrapure water until no solvent was detected in the filtrate. The volume ratio of dialysate (PBS or ultrapure water) and the residue used in the dialysis was maintained at >10:1 (v/v). The dialysis procedure was conducted for at least 10 days with the dialysate being replaced at least once a day. Dry products were obtained by lyophilization of the residue at room temperature, an internal pressure of less than 0.1 mbar and a cold trap of at less than −25° C.

The chemical compositions of the CD derivatives obtained were then determined by measuring the cyclodextrin content, the bound sulphate content, the total lipid content, the free lipid content and the bound lipid content (calculated by subtracting the free lipid content from the total lipid content), as described in Hilgers et al., VACCINE 12, 653–660 (1994).

The composition of the CD derivatives were expressed as the mean number of bound sulphate groups per molecule of the cyclodextrin derivatives produced and the mean number of bound lipid groups per molecule of the cyclodextrin derivatives produced.

The composition of the mean numbers of bound sulphate groups and bound lipid groups per molecule of the cyclodextrin derivatives produced are summarized in Table 1.

TABLE 1

Chemical Composition of CD Derivative Solution

| Solution designation | # of Grams of chlorosulphonic acid added | # of Grams of lauroylchloride added | Mean sulfate ratio[1] | Mean lipid ration[2] |
|---|---|---|---|---|
| Solution # 1 | 0.29 | 1.38 | 0.70 | 2.80 |
| Solution # 2 | 0.29 | 2.75 | 1.05 | 4.20 |
| Solution # 3 | 0.29 | 4.13 | 0.98 | 6.72 |
| Solution # 4 | 0.29 | 5.50 | 0.49 | 8.89 |
| Solution # 5 | 0.29 | 6.88 | 0.35 | 14.00 |
| Solution # 6 | 0.59 | 1.38 | 1.12 | 3.22 |
| Solution # 7 | 0.59 | 2.75 | 1.68 | 5.04 |
| Solution # 8 | 0.59 | 4.13 | 1.89 | 6.16 |
| Solution # 9 | 0.59 | 5.50 | 2.03 | 9.31 |
| Solution # 10 | 0.59 | 6.88 | 0.77 | 15.40 |
| Solution # 11 | 0.88 | 1.38 | 1.47 | 2.38 |
| Solution # 12 | 0.88 | 2.75 | 2.10 | 3.99 |
| Solution # 13 | 0.88 | 4.13 | 2.45 | 5.39 |
| Solution # 14 | 0.88 | 5.50 | 2.59 | 7.63 |
| Solution # 15 | 0.88 | 6.88 | 1.89 | 9.66 |
| Solution # 16 | 1.17 | 1.38 | 2.52 | 2.59 |
| Solution # 17 | 1.17 | 2.75 | 2.08 | 3.08 |
| Solution # 18 | 1.17 | 4.13 | 3.31 | 5.39 |
| Solution # 19 | 1.17 | 5.50 | 3.50 | 7.70 |
| Solution # 20 | 1.17 | 6.88 | 2.66 | 11.69 |

From the results presented in Table 1, the precise distribution of the different CD derivatives of the present invention which are present in the various solutions prepared by the use of the method of the present invention may be calculated by using the formula:

% of cyclodextrin derivative produced = $P(X) \cdot P(Y) \cdot 100$ $$\text{wherein } P(X) = \frac{e^{-(\text{mean sulfate ratio})} \cdot (\text{mean sulfate ratio})^X}{X!}$$

wherein X = real number of sulfate groups per CD molecule and wherein e = the base value of natural log (ln) and wherein, when the mean lipid ratio is $\leq N/2$ and N is the total number of hydroxyl groups per cyclodextrin molecule from which the derivatives were obtained, $$P(Y) = \frac{e^{-(\text{mean lipid ratio})} \cdot (\text{mean lipid ratio})^Y}{Y!}$$

wherein Y = real number of lipid groups per CD molecule; and wherein e = the base value of natural log (ln);

or, when the mean lipid ratio is $> N/2$ and N is the total number of hydroxyl groups per cyclodextrin molecule from which the derivatives were obtained $$P(Y) = \frac{e^{-(N-\text{mean lipid ratio})} \cdot (N - \text{mean lipid ratio})^{(N-Y)}}{(N-Y)!}$$

wherein Y = real number of lipid groups per CD molecule and wherein e = the base value of natural log (ln); and wherein N = the total number of hydroxyl groups per molecule of cyclodextrin from which the derivatives were obtained.

In this fashion the precise distribution the different CD derivatives of the present invention which are present in the respective solutions prepared by the use of the method of the present invention, as described above in this Example, are set forth as follows in Tables 2–21:

TABLE 2 mean sulphate ratio: 0.70
mean lipid ratio: 2.80

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 3.02 | 2.11 | 0.74 | 0.17 | 0.03 | 0.00 | 0.00 | 0.00 | 0.00 | 0.00 | 0.00 |
| 1 | 8.46 | 5.92 | 2.07 | 0.48 | 0.08 | 0.01 | 0.00 | 0.00 | 0.00 | 0.00 | 0.00 |
| 2 | 11.84 | 8.29 | 2.90 | 0.68 | 0.12 | 0.02 | 0.00 | 0.00 | 0.00 | 0.00 | 0.00 |
| 3 | 11.05 | 7.73 | 2.71 | 0.63 | 0.11 | 0.02 | 0.00 | 0.00 | 0.00 | 0.00 | 0.00 |
| 4 | 7.73 | 5.41 | 1.89 | 0.44 | 0.08 | 0.01 | 0.00 | 0.00 | 0.00 | 0.00 | 0.00 |
| 5 | 4.33 | 3.03 | 1.06 | 0.25 | 0.04 | 0.01 | 0.00 | 0.00 | 0.00 | 0.00 | 0.00 |
| 6 | 2.02 | 1.41 | 0.50 | 0.12 | 0.02 | 0.00 | 0.00 | 0.00 | 0.00 | 0.00 | 0.00 |
| 7 | 0.81 | 0.57 | 0.20 | 0.05 | 0.01 | 0.00 | 0.00 | 0.00 | 0.00 | 0.00 | 0.00 |
| 8 | 0.28 | 0.20 | 0.07 | 0.02 | 0.00 | 0.00 | 0.00 | 0.00 | 0.00 | 0.00 | 0.00 |
| 9 | 0.09 | 0.06 | 0.02 | 0.01 | 0.00 | 0.00 | 0.00 | 0.00 | 0.00 | 0.00 | 0.00 |
| 10 | 0.02 | 0.02 | 0.01 | 0.00 | 0.00 | 0.00 | 0.00 | 0.00 | 0.00 | 0.00 | 0.00 |
| 11 | 0.01 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |

TABLE 2-continued mean sulphate ratio: 0.70
mean lipid ratio: 2.80

| | | | | | | | | | | | |
|---|---|---|---|---|---|---|---|---|---|---|---|
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 3 mean sulphate ratio: 1.05
mean lipid ratio: 4.20

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.74 | 0.52 | 0.18 | 0.04 | 0.01 | 0.00 | 0.00 | 0.00 | 0.00 | 0.00 | 0.00 |
| 1 | 3.13 | 2.19 | 0.77 | 0.18 | 0.03 | 0.00 | 0.00 | 0.00 | 0.00 | 0.00 | 0.00 |
| 2 | 6.57 | 4.60 | 1.61 | 0.38 | 0.07 | 0.01 | 0.00 | 0.00 | 0.00 | 0.00 | 0.00 |
| 3 | 9.20 | 6.44 | 2.25 | 0.53 | 0.09 | 0.01 | 0.00 | 0.00 | 0.00 | 0.00 | 0.00 |
| 4 | 9.65 | 6.76 | 2.37 | 0.55 | 0.10 | 0.01 | 0.00 | 0.00 | 0.00 | 0.00 | 0.00 |
| 5 | 8.11 | 5.68 | 1.99 | 0.46 | 0.08 | 0.01 | 0.00 | 0.00 | 0.00 | 0.00 | 0.00 |
| 6 | 5.68 | 3.97 | 1.39 | 0.32 | 0.06 | 0.01 | 0.00 | 0.00 | 0.00 | 0.00 | 0.00 |
| 7 | 3.41 | 2.38 | 0.83 | 0.19 | 0.03 | 0.00 | 0.00 | 0.00 | 0.00 | 0.00 | 0.00 |
| 8 | 1.79 | 1.25 | 0.44 | 0.10 | 0.02 | 0.00 | 0.00 | 0.00 | 0.00 | 0.00 | 0.00 |
| 9 | 0.83 | 0.58 | 0.20 | 0.05 | 0.01 | 0.00 | 0.00 | 0.00 | 0.00 | 0.00 | 0.00 |
| 10 | 0.35 | 0.35 | 0.09 | 0.02 | 0.00 | 0.00 | 0.00 | 0.00 | 0.00 | 0.00 | 0.00 |
| 11 | 0.13 | 0.09 | 0.03 | 0.01 | 0.00 | 0.00 | 0.00 | 0.00 | 0.00 | 0.00 | 0.00 |
| 12 | 0.05 | 0.03 | 0.01 | 0.00 | 0.00 | 0.00 | 0.00 | 0.00 | 0.00 | 0.00 | 0.00 |
| 13 | 0.02 | 0.01 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

Number

TABLE 3-continued mean sulphate ratio: 1.05
mean lipid ratio: 4.20

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 4 mean sulphate ratio: 0.98
mean lipid ratio: 6.72

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.06 | 0.04 | 0.01 | 0.00 | 0.00 | 0.00 | 0.00 | 0.00 | 0.00 | 0.00 | 0.00 |
| 1 | 0.40 | 0.28 | 0.10 | 0.02 | 0.00 | 0.00 | 0.00 | 0.00 | 0.00 | 0.00 | 0.00 |
| 2 | 1.35 | 0.95 | 0.33 | 0.18 | 0.01 | 0.00 | 0.00 | 0.00 | 0.00 | 0.00 | 0.00 |
| 3 | 3.03 | 2.12 | 0.74 | 0.17 | 0.03 | 0.00 | 0.00 | 0.00 | 0.00 | 0.00 | 0.00 |
| 4 | 5.09 | 3.56 | 1.25 | 0.29 | 0.05 | 0.01 | 0.00 | 0.00 | 0.00 | 0.00 | 0.00 |
| 5 | 6.84 | 4.79 | 1.68 | 0.39 | 0.07 | 0.01 | 0.00 | 0.00 | 0.00 | 0.00 | 0.00 |
| 6 | 7.66 | 5.36 | 1.88 | 0.44 | 0.08 | 0.01 | 0.00 | 0.00 | 0.00 | 0.00 | 0.00 |
| 7 | 7.36 | 5.15 | 1.80 | 0.42 | 0.07 | 0.01 | 0.00 | 0.00 | 0.00 | 0.00 | 0.00 |
| 8 | 6.18 | 4.33 | 1.51 | 0.35 | 0.06 | 0.01 | 0.00 | 0.00 | 0.00 | 0.00 | 0.00 |
| 9 | 4.61 | 3.23 | 1.13 | 0.26 | 0.05 | 0.01 | 0.00 | 0.00 | 0.00 | 0.00 | 0.00 |
| 10 | 3.10 | 2.17 | 0.76 | 0.18 | 0.03 | 0.00 | 0.00 | 0.00 | 0.00 | 0.00 | 0.00 |
| 11 | 1.89 | 1.33 | 0.46 | 0.11 | 0.02 | 0.00 | 0.00 | 0.00 | 0.00 | 0.00 | 0.00 |
| 12 | 1.06 | 0.74 | 0.26 | 0.06 | 0.01 | 0.00 | 0.00 | 0.00 | 0.00 | 0.00 | 0.00 |
| 13 | 0.55 | 0.38 | 0.13 | 0.03 | 0.01 | 0.00 | 0.00 | 0.00 | 0.00 | 0.00 | 0.00 |
| 14 | 0.26 | 0.18 | 0.06 | 0.02 | 0.00 | 0.00 | 0.00 | 0.00 | 0.00 | 0.00 | 0.00 |
| 15 | 0.12 | 0.08 | 0.03 | 0.01 | 0.00 | 0.00 | 0.00 | 0.00 | 0.00 | 0.00 | 0.00 |
| 16 | 0.05 | 0.03 | 0.01 | 0.00 | 0.00 | 0.00 | 0.00 | 0.00 | 0.00 | 0.00 | 0.00 |
| 17 | 0.02 | 0.01 | 0.00 | 0.00 | 0.00 | 0.00 | 0.00 | 0.00 | 0.00 | 0.00 | 0.00 |
| 18 | 0.01 | 0.01 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |

TABLE 4-continued mean sulphate ratio: 0.98
mean lipid ratio: 6.72

| | | | | | | | | | | | |
|---|---|---|---|---|---|---|---|---|---|---|---|
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 5 mean sulphate ratio: 0.49
mean lipid ratio: 8.89

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.01 | 0.00 | 0.00 | 0.00 | 0.00 | 0.00 | 0.00 | 0.00 | 0.00 | 0.00 | 0.00 |
| 1 | 0.06 | 0.04 | 0.01 | 0.00 | 0.00 | 0.00 | 0.00 | 0.00 | 0.00 | 0.00 | 0.00 |
| 2 | 0.27 | 0.19 | 0.07 | 0.02 | 0.00 | 0.00 | 0.00 | 0.00 | 0.00 | 0.00 | 0.00 |
| 3 | 0.80 | 0.56 | 0.20 | 0.05 | 0.01 | 0.00 | 0.00 | 0.00 | 0.00 | 0.00 | 0.00 |
| 4 | 1.78 | 1.25 | 0.44 | 0.10 | 0.02 | 0.00 | 0.00 | 0.00 | 0.00 | 0.00 | 0.00 |
| 5 | 3.17 | 2.22 | 0.78 | 0.18 | 0.03 | 0.00 | 0.00 | 0.00 | 0.00 | 0.00 | 0.00 |
| 6 | 4.69 | 3.28 | 1.15 | 0.27 | 0.05 | 0.01 | 0.00 | 0.00 | 0.00 | 0.00 | 0.00 |
| 7 | 5.96 | 4.17 | 1.46 | 0.34 | 0.06 | 0.01 | 0.00 | 0.00 | 0.00 | 0.00 | 0.00 |
| 8 | 6.62 | 4.63 | 1.62 | 0.38 | 0.07 | 0.01 | 0.00 | 0.00 | 0.00 | 0.00 | 0.00 |
| 9 | 6.64 | 4.58 | 1.60 | 0.37 | 0.07 | 0.01 | 0.00 | 0.00 | 0.00 | 0.00 | 0.00 |
| 10 | 5.81 | 4.07 | 1.42 | 0.33 | 0.06 | 0.01 | 0.00 | 0.00 | 0.00 | 0.00 | 0.00 |
| 11 | 4.70 | 3.23 | 1.15 | 0.27 | 0.05 | 0.01 | 0.00 | 0.00 | 0.00 | 0.00 | 0.00 |
| 12 | 3.48 | 2.44 | 0.85 | 0.20 | 0.03 | 0.00 | 0.00 | 0.00 | 0.00 | 0.00 | 0.00 |
| 13 | 2.38 | 1.67 | 0.58 | 0.14 | 0.02 | 0.00 | 0.00 | 0.00 | 0.00 | 0.00 | 0.00 |
| 14 | 1.51 | 1.06 | 0.37 | 0.09 | 0.02 | 0.00 | 0.00 | 0.00 | 0.00 | 0.00 | 0.00 |
| 15 | 0.90 | 0.63 | 0.22 | 0.05 | 0.01 | 0.00 | 0.00 | 0.00 | 0.00 | 0.00 | 0.00 |
| 16 | 0.50 | 0.35 | 0.12 | 0.03 | 0.00 | 0.00 | 0.00 | 0.00 | 0.00 | 0.00 | 0.00 |
| 17 | 0.26 | 0.18 | 0.06 | 0.01 | 0.00 | 0.00 | 0.00 | 0.00 | 0.00 | 0.00 | 0.00 |
| 18 | 0.13 | 0.09 | 0.03 | 0.01 | 0.00 | 0.00 | 0.00 | 0.00 | 0.00 | 0.00 | 0.00 |
| 19 | 0.06 | 0.04 | 0.01 | 0.00 | 0.00 | 0.00 | 0.00 | 0.00 | 0.00 | 0.00 | 0.00 |
| 20 | 0.03 | 0.02 | 0.01 | 0.00 | 0.00 | 0.00 | 0.00 | 0.00 | 0.00 | 0.00 | 0.00 |
| 21 | 0.01 | 0.01 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |

TABLE 5-continued mean sulphate ratio: 0.49
mean lipid ratio: 8.89

| | | | | | | | | | | | |
|---|---|---|---|---|---|---|---|---|---|---|---|
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 6 mean sulphate ratio: 0.35
mean lipid ratio: 14.00

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.01 | 0.01 | 0.00 | 0.00 | 0.00 | 0.00 | 0.00 | 0.00 | 0.00 | 0.00 | 0.00 |
| 4 | 0.03 | 0.02 | 0.01 | 0.00 | 0.00 | 0.00 | 0.00 | 0.00 | 0.00 | 0.00 | 0.00 |
| 5 | 0.07 | 0.05 | 0.02 | 0.00 | 0.00 | 0.00 | 0.00 | 0.00 | 0.00 | 0.00 | 0.00 |
| 6 | 0.16 | 0.12 | 0.04 | 0.01 | 0.00 | 0.00 | 0.00 | 0.00 | 0.00 | 0.00 | 0.00 |
| 7 | 0.35 | 0.25 | 0.09 | 0.02 | 0.00 | 0.00 | 0.00 | 0.00 | 0.00 | 0.00 | 0.00 |
| 8 | 0.70 | 0.49 | 0.17 | 0.04 | 0.01 | 0.00 | 0.00 | 0.00 | 0.00 | 0.00 | 0.00 |
| 9 | 1.31 | 0.92 | 0.32 | 0.07 | 0.01 | 0.00 | 0.00 | 0.00 | 0.00 | 0.00 | 0.00 |
| 10 | 2.24 | 1.57 | 0.55 | 0.13 | 0.02 | 0.00 | 0.00 | 0.00 | 0.00 | 0.00 | 0.00 |
| 11 | 3.52 | 2.47 | 0.86 | 0.20 | 0.04 | 0.00 | 0.00 | 0.00 | 0.00 | 0.00 | 0.00 |
| 12 | 5.04 | 3.52 | 1.23 | 0.29 | 0.05 | 0.01 | 0.00 | 0.00 | 0.00 | 0.00 | 0.00 |
| 13 | 6.47 | 4.53 | 1.59 | 0.37 | 0.06 | 0.01 | 0.00 | 0.00 | 0.00 | 0.00 | 0.00 |
| 14 | 7.40 | 5.18 | 1.81 | 0.42 | 0.07 | 0.01 | 0.00 | 0.00 | 0.00 | 0.00 | 0.00 |
| 15 | 7.40 | 5.18 | 1.81 | 0.42 | 0.07 | 0.01 | 0.00 | 0.00 | 0.00 | 0.00 | 0.00 |
| 16 | 6.34 | 4.44 | 1.55 | 0.36 | 0.06 | 0.01 | 0.00 | 0.00 | 0.00 | 0.00 | 0.00 |
| 17 | 4.53 | 3.17 | 1.11 | 0.26 | 0.05 | 0.01 | 0.00 | 0.00 | 0.00 | 0.00 | 0.00 |
| 18 | 2.59 | 1.81 | 0.63 | 0.15 | 0.03 | 0.00 | 0.00 | 0.00 | 0.00 | 0.00 | 0.00 |
| 19 | 1.11 | 0.78 | 0.27 | 0.06 | 0.01 | 0.00 | 0.00 | 0.00 | 0.00 | 0.00 | 0.00 |
| 20 | 0.32 | 0.22 | 0.08 | 0.02 | 0.00 | 0.00 | 0.00 | 0.00 | 0.00 | 0.00 | 0.00 |
| 21 | 0.05 | 0.03 | 0.01 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 7 mean sulphate ratio: 1.12
mean lipid ratio: 3.22

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 1.98 | 1.39 | 0.49 | 0.11 | 0.02 | 0.00 | 0.00 | 0.00 | 0.00 | 0.00 | 0.00 |
| 1 | 6.32 | 4.47 | 1.57 | 0.37 | 0.06 | 0.01 | 0.00 | 0.00 | 0.00 | 0.00 | 0.00 |
| 2 | 10.29 | 7.20 | 2.52 | 0.59 | 0.10 | 0.01 | 0.00 | 0.00 | 0.00 | 0.00 | 0.00 |
| 3 | 11.04 | 7.73 | 2.70 | 0.63 | 0.11 | 0.02 | 0.00 | 0.00 | 0.00 | 0.00 | 0.00 |
| 4 | 8.89 | 6.22 | 2.18 | 0.51 | 0.09 | 0.01 | 0.00 | 0.00 | 0.00 | 0.00 | 0.00 |
| 5 | 5.72 | 4.01 | 1.40 | 0.33 | 0.06 | 0.01 | 0.00 | 0.00 | 0.00 | 0.00 | 0.00 |
| 6 | 3.07 | 2.15 | 0.75 | 0.18 | 0.03 | 0.00 | 0.00 | 0.00 | 0.00 | 0.00 | 0.00 |
| 7 | 1.41 | 0.99 | 0.35 | 0.08 | 0.01 | 0.00 | 0.00 | 0.00 | 0.00 | 0.00 | 0.00 |
| 8 | 0.57 | 0.40 | 0.14 | 0.03 | 0.01 | 0.00 | 0.00 | 0.00 | 0.00 | 0.00 | 0.00 |
| 9 | 0.20 | 0.14 | 0.05 | 0.01 | 0.00 | 0.00 | 0.00 | 0.00 | 0.00 | 0.00 | 0.00 |
| 10 | 0.07 | 0.05 | 0.02 | 0.00 | 0.00 | 0.00 | 0.00 | 0.00 | 0.00 | 0.00 | 0.00 |
| 11 | 0.02 | 0.01 | 0.00 | 0.00 | 0.00 | 0.00 | 0.00 | 0.00 | 0.00 | 0.00 | 0.00 |
| 12 | 0.01 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 8 mean sulphate ratio: 1.68
mean lipid ratio: 5.04

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.32 | 0.23 | 0.08 | 0.02 | 0.00 | 0.00 | 0.00 | 0.00 | 0.00 | 0.00 | 0.00 |
| 1 | 1.62 | 1.13 | 0.40 | 0.09 | 0.02 | 0.00 | 0.00 | 0.00 | 0.00 | 0.00 | 0.00 |
| 2 | 4.08 | 2.86 | 1.00 | 0.23 | 0.04 | 0.01 | 0.00 | 0.00 | 0.00 | 0.00 | 0.00 |
| 3 | 6.86 | 4.80 | 1.68 | 0.39 | 0.07 | 0.01 | 0.00 | 0.00 | 0.00 | 0.00 | 0.00 |

TABLE 8-continued mean sulphate ratio: 1.68
mean lipid ratio: 5.04

| | | | | | | | | | | | |
|---|---|---|---|---|---|---|---|---|---|---|---|
| 4 | 8.64 | 6.05 | 2.12 | 0.49 | 0.09 | 0.01 | 0.00 | 0.00 | 0.00 | 0.00 | 0.00 |
| 5 | 8.71 | 6.10 | 2.13 | 0.50 | 0.09 | 0.01 | 0.00 | 0.00 | 0.00 | 0.00 | 0.00 |
| 6 | 7.32 | 5.12 | 1.79 | 0.42 | 0.07 | 0.01 | 0.00 | 0.00 | 0.00 | 0.00 | 0.00 |
| 7 | 5.27 | 3.69 | 1.29 | 0.30 | 0.05 | 0.01 | 0.00 | 0.00 | 0.00 | 0.00 | 0.00 |
| 8 | 3.32 | 2.32 | 0.81 | 0.10 | 0.03 | 0.00 | 0.00 | 0.00 | 0.00 | 0.00 | 0.00 |
| 9 | 1.86 | 1.30 | 0.46 | 0.11 | 0.02 | 0.00 | 0.00 | 0.00 | 0.00 | 0.00 | 0.00 |
| 10 | 0.94 | 0.66 | 0.23 | 0.05 | 0.01 | 0.00 | 0.00 | 0.00 | 0.00 | 0.00 | 0.00 |
| 11 | 0.43 | 0.30 | 0.11 | 0.02 | 0.00 | 0.00 | 0.00 | 0.00 | 0.00 | 0.00 | 0.00 |
| 12 | 0.18 | 0.13 | 0.04 | 0.01 | 0.00 | 0.00 | 0.00 | 0.00 | 0.00 | 0.00 | 0.00 |
| 13 | 0.07 | 0.05 | 0.02 | 0.00 | 0.00 | 0.00 | 0.00 | 0.00 | 0.00 | 0.00 | 0.00 |
| 14 | 0.03 | 0.02 | 0.01 | 0.00 | 0.00 | 0.00 | 0.00 | 0.00 | 0.00 | 0.00 | 0.00 |
| 15 | 0.01 | 0.01 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 9 mean sulphate ratio: 1.89
mean lipid ratio: 6.16

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.10 | 0.07 | 0.03 | 0.01 | 0.00 | 0.00 | 0.00 | 0.00 | 0.00 | 0.00 | 0.00 |
| 1 | 0.65 | 0.45 | 0.16 | 0.04 | 0.01 | 0.00 | 0.00 | 0.00 | 0.00 | 0.00 | 0.00 |
| 2 | 1.99 | 1.39 | 0.49 | 0.11 | 0.02 | 0.00 | 0.00 | 0.00 | 0.00 | 0.00 | 0.00 |
| 3 | 4.09 | 2.86 | 1.00 | 0.23 | 0.04 | 0.01 | 0.00 | 0.00 | 0.00 | 0.00 | 0.00 |
| 4 | 6.29 | 4.41 | 1.54 | 0.36 | 0.06 | 0.01 | 0.00 | 0.00 | 0.00 | 0.00 | 0.00 |
| 5 | 7.75 | 5.43 | 1.90 | 0.44 | 0.08 | 0.01 | 0.00 | 0.00 | 0.00 | 0.00 | 0.00 |
| 6 | 7.96 | 5.57 | 1.95 | 0.46 | 0.08 | 0.01 | 0.00 | 0.00 | 0.00 | 0.00 | 0.00 |
| 7 | 7.00 | 4.90 | 1.72 | 0.40 | 0.07 | 0.01 | 0.00 | 0.00 | 0.00 | 0.00 | 0.00 |
| 8 | 5.39 | 3.78 | 1.32 | 0.31 | 0.05 | 0.01 | 0.00 | 0.00 | 0.00 | 0.00 | 0.00 |
| 9 | 3.69 | 2.58 | 0.00 | 0.21 | 0.04 | 0.00 | 0.00 | 0.00 | 0.00 | 0.00 | 0.00 |
| 10 | 2.27 | 1.59 | 0.56 | 0.13 | 0.02 | 0.00 | 0.00 | 0.00 | 0.00 | 0.00 | 0.00 |
| 11 | 1.27 | 0.89 | 0.31 | 0.07 | 0.01 | 0.00 | 0.00 | 0.00 | 0.00 | 0.00 | 0.00 |
| 12 | 0.65 | 0.46 | 0.16 | 0.04 | 0.01 | 0.00 | 0.00 | 0.00 | 0.00 | 0.00 | 0.00 |
| 13 | 0.31 | 0.22 | 0.08 | 0.02 | 0.00 | 0.00 | 0.00 | 0.00 | 0.00 | 0.00 | 0.00 |

TABLE 9-continued mean sulphate ratio: 1.89
mean lipid ratio: 6.16

| | | | | | | | | | | | |
|---|---|---|---|---|---|---|---|---|---|---|---|
| 14 | 0.14 | 0.10 | 0.03 | 0.01 | 0.00 | 0.00 | 0.00 | 0.00 | 0.00 | 0.00 | 0.00 |
| 15 | 0.06 | 0.04 | 0.01 | 0.00 | 0.00 | 0.00 | 0.00 | 0.00 | 0.00 | 0.00 | 0.00 |
| 16 | 0.02 | 0.02 | 0.01 | 0.00 | 0.00 | 0.00 | 0.00 | 0.00 | 0.00 | 0.00 | 0.00 |
| 17 | 0.01 | 0.01 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 10 mean sulphate ratio: 2.03
mean lipid ratio: 9.31

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.00 | 0.00 | 0.00 | 0.00 | 0.00 | 0.00 | 0.00 | 0.00 | 0.00 | 0.00 | 0.00 |
| 1 | 0.04 | 0.03 | 0.01 | 0.00 | 0.00 | 0.00 | 0.00 | 0.00 | 0.00 | 0.00 | 0.00 |
| 2 | 0.19 | 0.14 | 0.05 | 0.01 | 0.00 | 0.00 | 0.00 | 0.00 | 0.00 | 0.00 | 0.00 |
| 3 | 0.60 | 0.42 | 0.15 | 0.03 | 0.01 | 0.00 | 0.00 | 0.00 | 0.00 | 0.00 | 0.00 |
| 4 | 1.41 | 0.98 | 0.34 | 0.08 | 0.01 | 0.00 | 0.00 | 0.00 | 0.00 | 0.00 | 0.00 |
| 5 | 2.62 | 1.83 | 0.64 | 0.15 | 0.03 | 0.00 | 0.00 | 0.00 | 0.00 | 0.00 | 0.00 |
| 6 | 4.07 | 2.85 | 1.00 | 0.23 | 0.04 | 0.01 | 0.00 | 0.00 | 0.00 | 0.00 | 0.00 |
| 7 | 5.41 | 3.78 | 1.32 | 0.31 | 0.05 | 0.01 | 0.00 | 0.00 | 0.00 | 0.00 | 0.00 |
| 8 | 6.29 | 4.40 | 1.54 | 0.36 | 0.06 | 0.01 | 0.00 | 0.00 | 0.00 | 0.00 | 0.00 |
| 9 | 6.51 | 4.56 | 1.59 | 0.37 | 0.07 | 0.01 | 0.00 | 0.00 | 0.00 | 0.00 | 0.00 |
| 10 | 6.06 | 4.24 | 1.48 | 0.35 | 0.06 | 0.01 | 0.00 | 0.00 | 0.00 | 0.00 | 0.00 |
| 11 | 5.13 | 3.59 | 1.26 | 0.29 | 0.05 | 0.01 | 0.00 | 0.00 | 0.00 | 0.00 | 0.00 |
| 12 | 3.98 | 2.79 | 0.97 | 0.23 | 0.04 | 0.01 | 0.00 | 0.00 | 0.00 | 0.00 | 0.00 |
| 13 | 2.85 | 1.99 | 0.70 | 0.16 | 0.03 | 0.00 | 0.00 | 0.00 | 0.00 | 0.00 | 0.00 |
| 14 | 1.89 | 1.33 | 0.46 | 0.11 | 0.02 | 0.00 | 0.00 | 0.00 | 0.00 | 0.00 | 0.00 |
| 15 | 1.18 | 0.83 | 0.29 | 0.07 | 0.01 | 0.00 | 0.00 | 0.00 | 0.00 | 0.00 | 0.00 |
| 16 | 0.68 | 0.48 | 0.17 | 0.04 | 0.01 | 0.00 | 0.00 | 0.00 | 0.00 | 0.00 | 0.00 |
| 17 | 0.37 | 0.26 | 0.09 | 0.02 | 0.00 | 0.00 | 0.00 | 0.00 | 0.00 | 0.00 | 0.00 |
| 18 | 0.19 | 0.14 | 0.05 | 0.01 | 0.00 | 0.00 | 0.00 | 0.00 | 0.00 | 0.00 | 0.00 |
| 19 | 0.09 | 0.07 | 0.02 | 0.01 | 0.00 | 0.00 | 0.00 | 0.00 | 0.00 | 0.00 | 0.00 |
| 20 | 0.04 | 0.03 | 0.01 | 0.00 | 0.00 | 0.00 | 0.00 | 0.00 | 0.00 | 0.00 | 0.00 |
| 21 | 0.02 | 0.01 | 0.00 | 0.00 | 0.00 | 0.00 | 0.00 | 0.00 | 0.00 | 0.00 | 0.00 |

Number

TABLE 10-continued mean sulphate ratio: 2.03
mean lipid ratio: 9.31

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 11 mean sulphate ratio: 0.77
mean lipid ratio: 15.40

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.01 | 0.01 | 0.00 | 0.00 | 0.00 | 0.00 | 0.00 | 0.00 | 0.00 | 0.00 | 0.00 |
| 4 | 0.03 | 0.02 | 0.01 | 0.00 | 0.00 | 0.00 | 0.00 | 0.00 | 0.00 | 0.00 | 0.00 |
| 5 | 0.07 | 0.05 | 0.02 | 0.00 | 0.00 | 0.00 | 0.00 | 0.00 | 0.00 | 0.00 | 0.00 |
| 6 | 0.16 | 0.12 | 0.04 | 0.01 | 0.00 | 0.00 | 0.00 | 0.00 | 0.00 | 0.00 | 0.00 |
| 7 | 0.35 | 0.25 | 0.09 | 0.02 | 0.00 | 0.00 | 0.00 | 0.00 | 0.00 | 0.00 | 0.00 |
| 8 | 0.70 | 0.49 | 0.17 | 0.04 | 0.01 | 0.00 | 0.00 | 0.00 | 0.00 | 0.00 | 0.00 |
| 9 | 1.31 | 0.92 | 0.32 | 0.07 | 0.01 | 0.00 | 0.00 | 0.00 | 0.00 | 0.00 | 0.00 |
| 10 | 2.24 | 1.57 | 0.55 | 0.13 | 0.02 | 0.00 | 0.00 | 0.00 | 0.00 | 0.00 | 0.00 |
| 11 | 3.52 | 2.47 | 0.86 | 0.20 | 0.04 | 0.00 | 0.00 | 0.00 | 0.00 | 0.00 | 0.00 |
| 12 | 5.04 | 3.52 | 1.23 | 0.29 | 0.05 | 0.01 | 0.00 | 0.00 | 0.00 | 0.00 | 0.00 |
| 13 | 6.47 | 4.53 | 1.59 | 0.37 | 0.06 | 0.01 | 0.00 | 0.00 | 0.00 | 0.00 | 0.00 |
| 14 | 7.40 | 5.18 | 1.81 | 0.42 | 0.07 | 0.01 | 0.00 | 0.00 | 0.00 | 0.00 | 0.00 |
| 15 | 7.40 | 5.18 | 1.81 | 0.42 | 0.07 | 0.01 | 0.00 | 0.00 | 0.00 | 0.00 | 0.00 |
| 16 | 6.34 | 4.44 | 1.55 | 0.36 | 0.06 | 0.01 | 0.00 | 0.00 | 0.00 | 0.00 | 0.00 |
| 17 | 4.53 | 3.17 | 1.11 | 0.26 | 0.05 | 0.01 | 0.00 | 0.00 | 0.00 | 0.00 | 0.00 |
| 18 | 2.59 | 1.81 | 0.63 | 0.15 | 0.03 | 0.00 | 0.00 | 0.00 | 0.00 | 0.00 | 0.00 |
| 19 | 1.11 | 0.78 | 0.27 | 0.06 | 0.01 | 0.00 | 0.00 | 0.00 | 0.00 | 0.00 | 0.00 |
| 20 | 0.32 | 0.22 | 0.08 | 0.02 | 0.00 | 0.00 | 0.00 | 0.00 | 0.00 | 0.00 | 0.00 |
| 21 | 0.05 | 0.03 | 0.01 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |

TABLE 11-continued mean sulphate ratio: 0.77
mean lipid ratio: 15.40

| | | | | | | | | | | | |
|---|---|---|---|---|---|---|---|---|---|---|---|
| 5  | 0.00 | 0.00 | 0.00 | 0.00 | 0.00 | 0.00 | 0.00 | 0.00 | 0.00 | 0.00 | 0.00 |
| 6  | 0.00 | 0.00 | 0.00 | 0.00 | 0.00 | 0.00 | 0.00 | 0.00 | 0.00 | 0.00 | 0.00 |
| 7  | 0.00 | 0.00 | 0.00 | 0.00 | 0.00 | 0.00 | 0.00 | 0.00 | 0.00 | 0.00 | 0.00 |
| 8  | 0.00 | 0.00 | 0.00 | 0.00 | 0.00 | 0.00 | 0.00 | 0.00 | 0.00 | 0.00 | 0.00 |
| 9  | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 12 mean sulphate ratio: 1.47
mean lipid ratio: 2.38

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0  | 4.60  | 3.22 | 1.13 | 0.26 | 0.05 | 0.01 | 0.00 | 0.00 | 0.00 | 0.00 | 0.00 |
| 1  | 10.94 | 7.66 | 2.68 | 0.63 | 0.11 | 0.02 | 0.00 | 0.00 | 0.00 | 0.00 | 0.00 |
| 2  | 13.02 | 9.11 | 3.19 | 0.74 | 0.13 | 0.02 | 0.00 | 0.00 | 0.00 | 0.00 | 0.00 |
| 3  | 10.33 | 7.23 | 2.53 | 0.59 | 0.10 | 0.01 | 0.00 | 0.00 | 0.00 | 0.00 | 0.00 |
| 4  | 6.14  | 4.30 | 1.51 | 0.35 | 0.06 | 0.01 | 0.00 | 0.00 | 0.00 | 0.00 | 0.00 |
| 5  | 2.92  | 2.05 | 0.72 | 0.17 | 0.03 | 0.00 | 0.00 | 0.00 | 0.00 | 0.00 | 0.00 |
| 6  | 1.16  | 0.81 | 0.28 | 0.07 | 0.01 | 0.00 | 0.00 | 0.00 | 0.00 | 0.00 | 0.00 |
| 7  | 0.39  | 0.28 | 0.10 | 0.02 | 0.00 | 0.00 | 0.00 | 0.00 | 0.00 | 0.00 | 0.00 |
| 8  | 0.12  | 0.08 | 0.03 | 0.01 | 0.00 | 0.00 | 0.00 | 0.00 | 0.00 | 0.00 | 0.00 |
| 9  | 0.03  | 0.02 | 0.01 | 0.00 | 0.00 | 0.00 | 0.00 | 0.00 | 0.00 | 0.00 | 0.00 |
| 10 | 0.01  | 0.01 | 0.00 | 0.00 | 0.00 | 0.00 | 0.00 | 0.00 | 0.00 | 0.00 | 0.00 |
| 11 | 0.00  | 0.00 | 0.00 | 0.00 | 0.00 | 0.00 | 0.00 | 0.00 | 0.00 | 0.00 | 0.00 |
| 12 | 0.00  | 0.00 | 0.00 | 0.00 | 0.00 | 0.00 | 0.00 | 0.00 | 0.00 | 0.00 | 0.00 |
| 13 | 0.00  | 0.00 | 0.00 | 0.00 | 0.00 | 0.00 | 0.00 | 0.00 | 0.00 | 0.00 | 0.00 |
| 14 | 0.00  | 0.00 | 0.00 | 0.00 | 0.00 | 0.00 | 0.00 | 0.00 | 0.00 | 0.00 | 0.00 |
| 15 | 0.00  | 0.00 | 0.00 | 0.00 | 0.00 | 0.00 | 0.00 | 0.00 | 0.00 | 0.00 | 0.00 |
| 16 | 0.00  | 0.00 | 0.00 | 0.00 | 0.00 | 0.00 | 0.00 | 0.00 | 0.00 | 0.00 | 0.00 |
| 17 | 0.00  | 0.00 | 0.00 | 0.00 | 0.00 | 0.00 | 0.00 | 0.00 | 0.00 | 0.00 | 0.00 |
| 18 | 0.00  | 0.00 | 0.00 | 0.00 | 0.00 | 0.00 | 0.00 | 0.00 | 0.00 | 0.00 | 0.00 |
| 19 | 0.00  | 0.00 | 0.00 | 0.00 | 0.00 | 0.00 | 0.00 | 0.00 | 0.00 | 0.00 | 0.00 |
| 20 | 0.00  | 0.00 | 0.00 | 0.00 | 0.00 | 0.00 | 0.00 | 0.00 | 0.00 | 0.00 | 0.00 |
| 21 | 0.00  | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0  | 0.00 | 0.00 | 0.00 | 0.00 | 0.00 | 0.00 | 0.00 | 0.00 | 0.00 | 0.00 | 0.00 |
| 1  | 0.00 | 0.00 | 0.00 | 0.00 | 0.00 | 0.00 | 0.00 | 0.00 | 0.00 | 0.00 | 0.00 |
| 2  | 0.00 | 0.00 | 0.00 | 0.00 | 0.00 | 0.00 | 0.00 | 0.00 | 0.00 | 0.00 | 0.00 |
| 3  | 0.00 | 0.00 | 0.00 | 0.00 | 0.00 | 0.00 | 0.00 | 0.00 | 0.00 | 0.00 | 0.00 |
| 4  | 0.00 | 0.00 | 0.00 | 0.00 | 0.00 | 0.00 | 0.00 | 0.00 | 0.00 | 0.00 | 0.00 |
| 5  | 0.00 | 0.00 | 0.00 | 0.00 | 0.00 | 0.00 | 0.00 | 0.00 | 0.00 | 0.00 | 0.00 |
| 6  | 0.00 | 0.00 | 0.00 | 0.00 | 0.00 | 0.00 | 0.00 | 0.00 | 0.00 | 0.00 | 0.00 |
| 7  | 0.00 | 0.00 | 0.00 | 0.00 | 0.00 | 0.00 | 0.00 | 0.00 | 0.00 | 0.00 | 0.00 |
| 8  | 0.00 | 0.00 | 0.00 | 0.00 | 0.00 | 0.00 | 0.00 | 0.00 | 0.00 | 0.00 | 0.00 |
| 9  | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |

TABLE 12-continued mean sulphate ratio: 1.47
mean lipid ratio: 2.38

| | | | | | | | | | | | |
|---|---|---|---|---|---|---|---|---|---|---|---|
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 13 mean sulphate ratio: 2.10
mean lipid ratio: 3.99

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.92 | 0.64 | 0.23 | 0.05 | 0.01 | 0.00 | 0.00 | 0.00 | 0.00 | 0.00 | 0.00 |
| 1 | 3.67 | 2.57 | 0.90 | 0.21 | 0.04 | 0.01 | 0.00 | 0.00 | 0.00 | 0.00 | 0.00 |
| 2 | 7.31 | 5.12 | 1.79 | 0.42 | 0.07 | 0.01 | 0.00 | 0.00 | 0.00 | 0.00 | 0.00 |
| 3 | 9.73 | 6.81 | 2.38 | 0.56 | 0.10 | 0.01 | 0.00 | 0.00 | 0.00 | 0.00 | 0.00 |
| 4 | 9.70 | 6.79 | 2.38 | 0.55 | 0.10 | 0.01 | 0.00 | 0.00 | 0.00 | 0.00 | 0.00 |
| 5 | 7.74 | 5.42 | 1.90 | 0.44 | 0.08 | 0.01 | 0.00 | 0.00 | 0.00 | 0.00 | 0.00 |
| 6 | 5.15 | 3.60 | 1.26 | 0.29 | 0.05 | 0.01 | 0.00 | 0.00 | 0.00 | 0.00 | 0.00 |
| 7 | 2.93 | 2.05 | 0.72 | 0.17 | 0.03 | 0.00 | 0.00 | 0.00 | 0.00 | 0.00 | 0.00 |
| 8 | 1.46 | 1.02 | 0.36 | 0.08 | 0.01 | 0.00 | 0.00 | 0.00 | 0.00 | 0.00 | 0.00 |
| 9 | 0.65 | 0.45 | 0.16 | 0.04 | 0.01 | 0.00 | 0.00 | 0.00 | 0.00 | 0.00 | 0.00 |
| 10 | 0.26 | 0.18 | 0.06 | 0.01 | 0.00 | 0.00 | 0.00 | 0.00 | 0.00 | 0.00 | 0.00 |
| 11 | 0.09 | 0.07 | 0.02 | 0.01 | 0.00 | 0.00 | 0.00 | 0.00 | 0.00 | 0.00 | 0.00 |
| 12 | 0.03 | 0.02 | 0.01 | 0.00 | 0.00 | 0.00 | 0.00 | 0.00 | 0.00 | 0.00 | 0.00 |
| 13 | 0.01 | 0.01 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 14 mean sulphate ratio: 2.45
mean lipid ratio: 5.39

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.23 | 0.16 | 0.06 | 0.01 | 0.00 | 0.00 | 0.00 | 0.00 | 0.00 | 0.00 | 0.00 |
| 1 | 1.22 | 0.85 | 0.30 | 0.07 | 0.01 | 0.00 | 0.00 | 0.00 | 0.00 | 0.00 | 0.00 |
| 2 | 3.29 | 2.30 | 0.81 | 0.19 | 0.03 | 0.00 | 0.00 | 0.00 | 0.00 | 0.00 | 0.00 |
| 3 | 5.91 | 4.14 | 1.45 | 0.34 | 0.06 | 0.01 | 0.00 | 0.00 | 0.00 | 0.00 | 0.00 |
| 4 | 7.79 | 5.58 | 1.95 | 0.46 | 0.08 | 0.01 | 0.00 | 0.00 | 0.00 | 0.00 | 0.00 |
| 5 | 8.59 | 6.01 | 2.10 | 0.49 | 0.09 | 0.01 | 0.00 | 0.00 | 0.00 | 0.00 | 0.00 |
| 6 | 7.72 | 5.40 | 1.89 | 0.44 | 0.08 | 0.01 | 0.00 | 0.00 | 0.00 | 0.00 | 0.00 |
| 7 | 5.94 | 4.16 | 1.46 | 0.34 | 0.06 | 0.01 | 0.00 | 0.00 | 0.00 | 0.00 | 0.00 |
| 8 | 4.00 | 2.80 | 0.98 | 0.23 | 0.04 | 0.01 | 0.00 | 0.00 | 0.00 | 0.00 | 0.00 |
| 9 | 2.40 | 1.68 | 0.59 | 0.14 | 0.02 | 0.00 | 0.00 | 0.00 | 0.00 | 0.00 | 0.00 |
| 10 | 1.29 | 0.90 | 0.32 | 0.07 | 0.01 | 0.00 | 0.00 | 0.00 | 0.00 | 0.00 | 0.00 |
| 11 | 0.63 | 0.44 | 0.16 | 0.04 | 0.01 | 0.00 | 0.00 | 0.00 | 0.00 | 0.00 | 0.00 |
| 12 | 0.28 | 0.20 | 0.07 | 0.02 | 0.00 | 0.00 | 0.00 | 0.00 | 0.00 | 0.00 | 0.00 |
| 13 | 0.12 | 0.08 | 0.03 | 0.01 | 0.00 | 0.00 | 0.00 | 0.00 | 0.00 | 0.00 | 0.00 |
| 14 | 0.05 | 0.03 | 0.01 | 0.00 | 0.00 | 0.00 | 0.00 | 0.00 | 0.00 | 0.00 | 0.00 |
| 15 | 0.02 | 0.01 | 0.00 | 0.00 | 0.00 | 0.00 | 0.00 | 0.00 | 0.00 | 0.00 | 0.00 |
| 16 | 0.01 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 15 mean sulphate ratio: 2.59
mean lipid ratio: 7.63

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.02 | 0.02 | 0.01 | 0.00 | 0.00 | 0.00 | 0.00 | 0.00 | 0.00 | 0.00 | 0.00 |
| 1 | 0.18 | 0.13 | 0.05 | 0.01 | 0.01 | 0.00 | 0.00 | 0.00 | 0.00 | 0.00 | 0.00 |
| 2 | 0.70 | 0.49 | 0.17 | 0.04 | 0.02 | 0.00 | 0.00 | 0.00 | 0.00 | 0.00 | 0.00 |
| 3 | 1.79 | 1.25 | 0.44 | 0.10 | 0.03 | 0.00 | 0.00 | 0.00 | 0.00 | 0.00 | 0.00 |

TABLE 15-continued mean sulphate ratio: 2.59
mean lipid ratio: 7.63

| | | | | | | | | | | | |
|---|---|---|---|---|---|---|---|---|---|---|---|
| 4 | 3.41 | 2.38 | 0.83 | 0.19 | 0.05 | 0.00 | 0.00 | 0.00 | 0.00 | 0.00 | 0.00 |
| 5 | 5.20 | 3.64 | 1.27 | 0.30 | 0.07 | 0.01 | 0.00 | 0.00 | 0.00 | 0.00 | 0.00 |
| 6 | 6.61 | 4.63 | 1.62 | 0.38 | 0.07 | 0.01 | 0.00 | 0.00 | 0.00 | 0.00 | 0.00 |
| 7 | 7.20 | 5.04 | 1.76 | 0.41 | 0.07 | 0.01 | 0.00 | 0.00 | 0.00 | 0.00 | 0.00 |
| 8 | 6.87 | 4.81 | 1.68 | 0.39 | 0.06 | 0.01 | 0.00 | 0.00 | 0.00 | 0.00 | 0.00 |
| 9 | 5.82 | 4.08 | 1.43 | 0.33 | 0.04 | 0.01 | 0.00 | 0.00 | 0.00 | 0.00 | 0.00 |
| 10 | 4.44 | 3.11 | 1.09 | 0.25 | 0.03 | 0.01 | 0.00 | 0.00 | 0.00 | 0.00 | 0.00 |
| 11 | 3.08 | 2.16 | 0.76 | 0.18 | 0.02 | 0.00 | 0.00 | 0.00 | 0.00 | 0.00 | 0.00 |
| 12 | 1.96 | 1.37 | 0.48 | 0.11 | 0.01 | 0.00 | 0.00 | 0.00 | 0.00 | 0.00 | 0.00 |
| 13 | 1.15 | 0.81 | 0.28 | 0.07 | 0.00 | 0.00 | 0.00 | 0.00 | 0.00 | 0.00 | 0.00 |
| 14 | 0.63 | 0.44 | 0.15 | 0.04 | 0.00 | 0.00 | 0.00 | 0.00 | 0.00 | 0.00 | 0.00 |
| 15 | 0.32 | 0.22 | 0.08 | 0.02 | 0.00 | 0.00 | 0.00 | 0.00 | 0.00 | 0.00 | 0.00 |
| 16 | 0.15 | 0.11 | 0.04 | 0.01 | 0.00 | 0.00 | 0.00 | 0.00 | 0.00 | 0.00 | 0.00 |
| 17 | 0.07 | 0.05 | 0.02 | 0.00 | 0.00 | 0.00 | 0.00 | 0.00 | 0.00 | 0.00 | 0.00 |
| 18 | 0.03 | 0.02 | 0.01 | 0.00 | 0.00 | 0.00 | 0.00 | 0.00 | 0.00 | 0.00 | 0.00 |
| 19 | 0.01 | 0.01 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 16 mean sulphate ratio: 1.89
mean lipid ratio: 9.66

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.00 | 0.00 | 0.00 | 0.00 | 0.00 | 0.00 | 0.00 | 0.00 | 0.00 | 0.00 | 0.00 |
| 1 | 0.03 | 0.02 | 0.01 | 0.00 | 0.00 | 0.00 | 0.00 | 0.00 | 0.00 | 0.00 | 0.00 |
| 2 | 0.15 | 0.10 | 0.04 | 0.01 | 0.00 | 0.00 | 0.00 | 0.00 | 0.00 | 0.00 | 0.00 |
| 3 | 0.48 | 0.33 | 0.12 | 0.03 | 0.00 | 0.00 | 0.00 | 0.00 | 0.00 | 0.00 | 0.00 |
| 4 | 1.15 | 0.80 | 0.28 | 0.07 | 0.01 | 0.00 | 0.00 | 0.00 | 0.00 | 0.00 | 0.00 |
| 5 | 2.22 | 1.55 | 0.54 | 0.13 | 0.02 | 0.00 | 0.00 | 0.00 | 0.00 | 0.00 | 0.00 |
| 6 | 3.57 | 2.50 | 0.88 | 0.20 | 0.04 | 0.01 | 0.00 | 0.00 | 0.00 | 0.00 | 0.00 |
| 7 | 4.93 | 3.45 | 1.21 | 0.28 | 0.05 | 0.01 | 0.00 | 0.00 | 0.00 | 0.00 | 0.00 |
| 8 | 5.96 | 4.17 | 1.46 | 0.34 | 0.06 | 0.01 | 0.00 | 0.00 | 0.00 | 0.00 | 0.00 |
| 9 | 6.39 | 4.48 | 1.57 | 0.37 | 0.06 | 0.01 | 0.00 | 0.00 | 0.00 | 0.00 | 0.00 |
| 10 | 6.18 | 4.32 | 1.51 | 0.35 | 0.06 | 0.01 | 0.00 | 0.00 | 0.00 | 0.00 | 0.00 |
| 11 | 5.42 | 3.80 | 1.33 | 0.31 | 0.05 | 0.01 | 0.00 | 0.00 | 0.00 | 0.00 | 0.00 |
| 12 | 4.37 | 3.06 | 1.07 | 0.25 | 0.04 | 0.01 | 0.00 | 0.00 | 0.00 | 0.00 | 0.00 |
| 13 | 3.24 | 2.27 | 0.79 | 0.19 | 0.03 | 0.00 | 0.00 | 0.00 | 0.00 | 0.00 | 0.00 |

TABLE 16-continued mean sulphate ratio: 1.89
mean lipid ratio: 9.66

| | | | | | | | | | | | |
|---|---|---|---|---|---|---|---|---|---|---|---|
| 14 | 2.24 | 1.57 | 0.55 | 0.13 | 0.02 | 0.00 | 0.00 | 0.00 | 0.00 | 0.00 | 0.00 |
| 15 | 1.44 | 1.01 | 0.35 | 0.08 | 0.01 | 0.00 | 0.00 | 0.00 | 0.00 | 0.00 | 0.00 |
| 16 | 0.87 | 0.61 | 0.21 | 0.05 | 0.01 | 0.00 | 0.00 | 0.00 | 0.00 | 0.00 | 0.00 |
| 17 | 0.49 | 0.35 | 0.12 | 0.03 | 0.00 | 0.00 | 0.00 | 0.00 | 0.00 | 0.00 | 0.00 |
| 18 | 0.27 | 0.19 | 0.07 | 0.02 | 0.00 | 0.00 | 0.00 | 0.00 | 0.00 | 0.00 | 0.00 |
| 19 | 0.13 | 0.09 | 0.03 | 0.01 | 0.00 | 0.00 | 0.00 | 0.00 | 0.00 | 0.00 | 0.00 |
| 20 | 0.07 | 0.05 | 0.02 | 0.00 | 0.00 | 0.00 | 0.00 | 0.00 | 0.00 | 0.00 | 0.00 |
| 21 | 0.03 | 0.02 | 0.01 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 17 mean sulphate ratio: 2.52
mean lipid ratio: 2.59

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 3.73 | 2.61 | 0.91 | 0.21 | 0.04 | 0.01 | 0.00 | 0.00 | 0.00 | 0.00 | 0.00 |
| 1 | 9.65 | 6.75 | 2.36 | 0.55 | 0.10 | 0.01 | 0.00 | 0.00 | 0.00 | 0.00 | 0.00 |
| 2 | 12.50 | 8.75 | 3.06 | 0.71 | 0.13 | 0.02 | 0.00 | 0.00 | 0.00 | 0.00 | 0.00 |
| 3 | 10.79 | 7.55 | 2.64 | 0.62 | 0.11 | 0.02 | 0.00 | 0.00 | 0.00 | 0.00 | 0.00 |
| 4 | 6.98 | 4.89 | 1.71 | 0.40 | 0.07 | 0.01 | 0.00 | 0.00 | 0.00 | 0.00 | 0.00 |
| 5 | 3.62 | 2.53 | 0.89 | 0.21 | 0.04 | 0.01 | 0.00 | 0.00 | 0.00 | 0.00 | 0.00 |
| 6 | 1.56 | 1.09 | 0.38 | 0.09 | 0.02 | 0.00 | 0.00 | 0.00 | 0.00 | 0.00 | 0.00 |
| 7 | 0.58 | 0.40 | 0.14 | 0.03 | 0.01 | 0.00 | 0.00 | 0.00 | 0.00 | 0.00 | 0.00 |
| 8 | 0.19 | 0.13 | 0.05 | 0.01 | 0.00 | 0.00 | 0.00 | 0.00 | 0.00 | 0.00 | 0.00 |
| 9 | 0.05 | 0.04 | 0.01 | 0.00 | 0.00 | 0.00 | 0.00 | 0.00 | 0.00 | 0.00 | 0.00 |
| 10 | 0.01 | 0.01 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

Number

TABLE 17-continued mean sulphate ratio: 2.52
mean lipid ratio: 2.59

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 18 mean sulphate ratio: 2.08
mean lipid ratio: 3.08

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 2.28 | 1.60 | 0.56 | 0.13 | 0.02 | 0.00 | 0.00 | 0.00 | 0.00 | 0.00 | 0.00 |
| 1 | 7.03 | 4.92 | 1.72 | 0.40 | 0.07 | 0.01 | 0.00 | 0.00 | 0.00 | 0.00 | 0.00 |
| 2 | 10.83 | 7.58 | 2.65 | 0.62 | 0.11 | 0.02 | 0.00 | 0.00 | 0.00 | 0.00 | 0.00 |
| 3 | 11.11 | 7.78 | 2.72 | 0.64 | 0.11 | 0.02 | 0.00 | 0.00 | 0.00 | 0.00 | 0.00 |
| 4 | 8.56 | 5.99 | 2.10 | 0.40 | 0.09 | 0.01 | 0.00 | 0.00 | 0.00 | 0.00 | 0.00 |
| 5 | 5.27 | 3.69 | 1.29 | 0.30 | 0.05 | 0.01 | 0.00 | 0.00 | 0.00 | 0.00 | 0.00 |
| 6 | 2.71 | 1.89 | 0.66 | 0.15 | 0.03 | 0.00 | 0.00 | 0.00 | 0.00 | 0.00 | 0.00 |
| 7 | 1.19 | 0.83 | 0.29 | 0.07 | 0.01 | 0.00 | 0.00 | 0.00 | 0.00 | 0.00 | 0.00 |
| 8 | 0.46 | 0.32 | 0.11 | 0.03 | 0.00 | 0.00 | 0.00 | 0.00 | 0.00 | 0.00 | 0.00 |
| 9 | 0.16 | 0.11 | 0.04 | 0.01 | 0.00 | 0.00 | 0.00 | 0.00 | 0.00 | 0.00 | 0.00 |
| 10 | 0.05 | 0.03 | 0.01 | 0.00 | 0.00 | 0.00 | 0.00 | 0.00 | 0.00 | 0.00 | 0.00 |
| 11 | 0.01 | 0.01 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |

TABLE 18-continued mean sulphate ratio: 2.08
mean lipid ratio: 3.08

| | | | | | | | | | | |
|---|---|---|---|---|---|---|---|---|---|---|
| 6 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 |

TABLE 19 mean sulphate ratio: 3.31
mean lipid ratio: 5.39

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.23 | 0.16 | 0.06 | 0.01 | 0.00 | 0.00 | 0.00 | 0.00 | 0.00 | 0.00 | 0.00 |
| 1 | 1.22 | 0.85 | 0.30 | 0.07 | 0.01 | 0.00 | 0.00 | 0.00 | 0.00 | 0.00 | 0.00 |
| 2 | 3.29 | 2.30 | 0.81 | 0.19 | 0.03 | 0.00 | 0.00 | 0.00 | 0.00 | 0.00 | 0.00 |
| 3 | 5.91 | 4.14 | 1.45 | 0.34 | 0.06 | 0.01 | 0.00 | 0.00 | 0.00 | 0.00 | 0.00 |
| 4 | 7.97 | 5.58 | 1.95 | 0.46 | 0.08 | 0.01 | 0.00 | 0.00 | 0.00 | 0.00 | 0.00 |
| 5 | 8.59 | 6.01 | 2.10 | 0.49 | 0.09 | 0.01 | 0.00 | 0.00 | 0.00 | 0.00 | 0.00 |
| 6 | 7.72 | 5.40 | 1.89 | 0.44 | 0.08 | 0.01 | 0.00 | 0.00 | 0.00 | 0.00 | 0.00 |
| 7 | 5.94 | 4.16 | 1.46 | 0.34 | 0.06 | 0.01 | 0.00 | 0.00 | 0.00 | 0.00 | 0.00 |
| 8 | 4.00 | 2.80 | 0.98 | 0.23 | 0.04 | 0.01 | 0.00 | 0.00 | 0.00 | 0.00 | 0.00 |
| 9 | 2.40 | 1.68 | 0.59 | 0.14 | 0.02 | 0.00 | 0.00 | 0.00 | 0.00 | 0.00 | 0.00 |
| 10 | 1.29 | 0.90 | 0.32 | 0.07 | 0.01 | 0.00 | 0.00 | 0.00 | 0.00 | 0.00 | 0.00 |
| 11 | 0.63 | 0.44 | 0.16 | 0.04 | 0.01 | 0.00 | 0.00 | 0.00 | 0.00 | 0.00 | 0.00 |
| 12 | 0.28 | 0.20 | 0.07 | 0.02 | 0.00 | 0.00 | 0.00 | 0.00 | 0.00 | 0.00 | 0.00 |
| 13 | 0.12 | 0.08 | 0.03 | 0.01 | 0.00 | 0.00 | 0.00 | 0.00 | 0.00 | 0.00 | 0.00 |
| 14 | 0.05 | 0.03 | 0.01 | 0.00 | 0.00 | 0.00 | 0.00 | 0.00 | 0.00 | 0.00 | 0.00 |
| 15 | 0.02 | 0.01 | 0.00 | 0.00 | 0.00 | 0.00 | 0.00 | 0.00 | 0.00 | 0.00 | 0.00 |
| 16 | 0.01 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |

TABLE 19-continued mean sulphate ratio: 3.31
mean lipid ratio: 5.39

| | | | | | | | | | | | |
|---|---|---|---|---|---|---|---|---|---|---|---|
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 20 mean sulphate ratio: 3.50
mean lipid ratio: 7.70

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.02 | 0.02 | 0.01 | 0.00 | 0.00 | 0.00 | 0.00 | 0.00 | 0.00 | 0.00 | 0.00 |
| 1 | 0.17 | 0.12 | 0.04 | 0.01 | 0.00 | 0.00 | 0.00 | 0.00 | 0.00 | 0.00 | 0.00 |
| 2 | 0.67 | 0.47 | 0.16 | 0.04 | 0.01 | 0.00 | 0.00 | 0.00 | 0.00 | 0.00 | 0.00 |
| 3 | 1.71 | 1.20 | 0.42 | 0.10 | 0.02 | 0.00 | 0.00 | 0.00 | 0.00 | 0.00 | 0.00 |
| 4 | 3.29 | 2.31 | 0.81 | 0.19 | 0.03 | 0.00 | 0.00 | 0.00 | 0.00 | 0.00 | 0.00 |
| 5 | 5.07 | 3.55 | 1.24 | 0.29 | 0.05 | 0.01 | 0.00 | 0.00 | 0.00 | 0.00 | 0.00 |
| 6 | 6.51 | 4.56 | 1.59 | 0.37 | 0.07 | 0.01 | 0.00 | 0.00 | 0.00 | 0.00 | 0.00 |
| 7 | 7.16 | 5.01 | 1.75 | 0.41 | 0.07 | 0.01 | 0.00 | 0.00 | 0.00 | 0.00 | 0.00 |
| 8 | 6.89 | 4.82 | 1.69 | 0.39 | 0.07 | 0.01 | 0.00 | 0.00 | 0.00 | 0.00 | 0.00 |
| 9 | 5.90 | 4.13 | 1.44 | 0.34 | 0.06 | 0.01 | 0.00 | 0.00 | 0.00 | 0.00 | 0.00 |
| 10 | 4.54 | 3.18 | 1.11 | 0.26 | 0.05 | 0.01 | 0.00 | 0.00 | 0.00 | 0.00 | 0.00 |
| 11 | 3.18 | 2.22 | 0.78 | 0.18 | 0.03 | 0.00 | 0.00 | 0.00 | 0.00 | 0.00 | 0.00 |
| 12 | 2.04 | 1.43 | 0.50 | 0.12 | 0.02 | 0.00 | 0.00 | 0.00 | 0.00 | 0.00 | 0.00 |
| 13 | 1.21 | 0.85 | 0.30 | 0.07 | 0.01 | 0.00 | 0.00 | 0.00 | 0.00 | 0.00 | 0.00 |
| 14 | 0.66 | 0.47 | 0.16 | 0.04 | 0.01 | 0.00 | 0.00 | 0.00 | 0.00 | 0.00 | 0.00 |
| 15 | 0.34 | 0.24 | 0.08 | 0.02 | 0.00 | 0.00 | 0.00 | 0.00 | 0.00 | 0.00 | 0.00 |
| 16 | 0.16 | 0.11 | 0.04 | 0.01 | 0.00 | 0.00 | 0.00 | 0.00 | 0.00 | 0.00 | 0.00 |
| 17 | 0.07 | 0.05 | 0.02 | 0.00 | 0.00 | 0.00 | 0.00 | 0.00 | 0.00 | 0.00 | 0.00 |
| 18 | 0.03 | 0.02 | 0.01 | 0.00 | 0.00 | 0.00 | 0.00 | 0.00 | 0.00 | 0.00 | 0.00 |
| 19 | 0.01 | 0.01 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 21 mean sulphate ratio: 2.66
mean lipid ratio: 11.69

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.01 | 0.01 | 0.00 | 0.00 | 0.00 | 0.00 | 0.00 | 0.00 | 0.00 | 0.00 | 0.00 |
| 4 | 0.03 | 0.02 | 0.01 | 0.00 | 0.00 | 0.00 | 0.00 | 0.00 | 0.00 | 0.00 | 0.00 |
| 5 | 0.07 | 0.05 | 0.02 | 0.00 | 0.00 | 0.00 | 0.00 | 0.00 | 0.00 | 0.00 | 0.00 |
| 6 | 0.16 | 0.12 | 0.04 | 0.01 | 0.00 | 0.00 | 0.00 | 0.00 | 0.00 | 0.00 | 0.00 |
| 7 | 0.35 | 0.25 | 0.09 | 0.02 | 0.00 | 0.00 | 0.00 | 0.00 | 0.00 | 0.00 | 0.00 |
| 8 | 0.70 | 0.49 | 0.17 | 0.04 | 0.01 | 0.00 | 0.00 | 0.00 | 0.00 | 0.00 | 0.00 |
| 9 | 1.31 | 0.92 | 0.32 | 0.07 | 0.01 | 0.00 | 0.00 | 0.00 | 0.00 | 0.00 | 0.00 |
| 10 | 2.24 | 1.57 | 0.55 | 0.13 | 0.02 | 0.00 | 0.00 | 0.00 | 0.00 | 0.00 | 0.00 |
| 11 | 3.52 | 2.47 | 0.86 | 0.20 | 0.04 | 0.00 | 0.00 | 0.00 | 0.00 | 0.00 | 0.00 |
| 12 | 5.04 | 3.52 | 1.23 | 0.29 | 0.05 | 0.01 | 0.00 | 0.00 | 0.00 | 0.00 | 0.00 |
| 13 | 6.47 | 4.53 | 1.59 | 0.37 | 0.06 | 0.01 | 0.00 | 0.00 | 0.00 | 0.00 | 0.00 |
| 14 | 7.40 | 5.18 | 1.81 | 0.42 | 0.07 | 0.01 | 0.00 | 0.00 | 0.00 | 0.00 | 0.00 |
| 15 | 7.40 | 5.18 | 1.81 | 0.42 | 0.07 | 0.01 | 0.00 | 0.00 | 0.00 | 0.00 | 0.00 |
| 16 | 6.34 | 4.44 | 1.55 | 0.36 | 0.06 | 0.01 | 0.00 | 0.00 | 0.00 | 0.00 | 0.00 |
| 17 | 4.53 | 3.17 | 1.11 | 0.26 | 0.05 | 0.01 | 0.00 | 0.00 | 0.00 | 0.00 | 0.00 |
| 18 | 2.59 | 1.81 | 0.63 | 0.15 | 0.03 | 0.00 | 0.00 | 0.00 | 0.00 | 0.00 | 0.00 |
| 19 | 1.11 | 0.78 | 0.27 | 0.06 | 0.01 | 0.00 | 0.00 | 0.00 | 0.00 | 0.00 | 0.00 |
| 20 | 0.32 | 0.22 | 0.08 | 0.02 | 0.00 | 0.00 | 0.00 | 0.00 | 0.00 | 0.00 | 0.00 |
| 21 | 0.05 | 0.03 | 0.01 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |

TABLE 21-continued mean sulphate ratio: 2.66
mean lipid ratio: 11.69

| | | | | | | | | | | | |
|---|---|---|---|---|---|---|---|---|---|---|---|
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

EXAMPLE 2

A composition of CD derivatives were produced (and the chemical compositions thereof were determined) in the same manner as described above in Example 1, but with the following exceptions: (1) that the anhydrous dimethylformamide/anhydrous pyridin mixture was a 4:3 (v/v) mixture of anhydrous dimethylformamide (4 parts) and anhydrous pyridin (3 parts); (2) that respective 280 gram samples of the dried CD was solubilized in respective 2000 ml samples of the anhydrous dimethylformamide/pyridin mixture; and (3) that the quantities of lauroylchloride and chlorosulphonic acid were altered to be those which are set forth below in Table 22:

TABLE 22

Chemical Composition of CD Derivative Solution

| Solution Designation | # of Grams of chlorosulphonic acid added | # of Grams of lauroylchloride added | Mean Sulfate Ratio[1] | Mean Lipid Ratio[2] |
|---|---|---|---|---|
| Solution # 21 | 41 | 510 | 1.40 | 7.70 |
| Solution # 22 | 48 | 504 | 1.40 | 7.00 |

TABLE 22-continued

Chemical Composition of CD Derivative Solution

| Solution Designation | # of Grams of chlorosulphonic acid added | # of Grams of lauroylchloride added | Mean Sulfate Ratio[1] | Mean Lipid Ratio[2] |
|---|---|---|---|---|
| Solution # 23 | 53 | 498 | 1.40 | 8.40 |

[1]Mean sulfate ratio is expressed as the mean number of bound sulphate groups per cyclodextrin molecule.
[2]Mean lipid ratio is expressed as the mean number of bound lipid groups per cyclodextrin molecule.

The precise distribution the different CD derivatives of the present invention which are present in the respective solutions prepared by the use of the method of the present invention, as described above in this Example, were determined using the same formula as described above in Example 1, the results thereof being set forth as follows in Tables 23–25:

TABLE 23 mean sulphate ratio: 1.40
mean lipid ratio: 7.70

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.02 | 0.02 | 0.01 | 0.00 | 0.00 | 0.00 | 0.00 | 0.00 | 0.00 | 0.00 | 0.00 |
| 1 | 0.17 | 0.12 | 0.04 | 0.01 | 0.00 | 0.00 | 0.00 | 0.00 | 0.00 | 0.00 | 0.00 |
| 2 | 0.67 | 0.47 | 0.16 | 0.04 | 0.01 | 0.00 | 0.00 | 0.00 | 0.00 | 0.00 | 0.00 |
| 3 | 1.71 | 1.20 | 0.42 | 0.10 | 0.02 | 0.00 | 0.00 | 0.00 | 0.00 | 0.00 | 0.00 |
| 4 | 3.29 | 2.31 | 0.81 | 0.19 | 0.03 | 0.00 | 0.00 | 0.00 | 0.00 | 0.00 | 0.00 |
| 5 | 5.07 | 3.55 | 1.24 | 0.29 | 0.05 | 0.01 | 0.00 | 0.00 | 0.00 | 0.00 | 0.00 |
| 6 | 6.51 | 4.56 | 1.59 | 0.37 | 0.07 | 0.01 | 0.00 | 0.00 | 0.00 | 0.00 | 0.00 |
| 7 | 7.16 | 5.01 | 1.75 | 0.41 | 0.07 | 0.01 | 0.00 | 0.00 | 0.00 | 0.00 | 0.00 |
| 8 | 6.89 | 4.82 | 1.69 | 0.39 | 0.07 | 0.01 | 0.00 | 0.00 | 0.00 | 0.00 | 0.00 |
| 9 | 5.90 | 4.13 | 1.44 | 0.34 | 0.06 | 0.01 | 0.00 | 0.00 | 0.00 | 0.00 | 0.00 |
| 10 | 4.54 | 3.18 | 1.11 | 0.26 | 0.05 | 0.01 | 0.00 | 0.00 | 0.00 | 0.00 | 0.00 |
| 11 | 3.18 | 2.22 | 0.78 | 0.18 | 0.03 | 0.00 | 0.00 | 0.00 | 0.00 | 0.00 | 0.00 |
| 12 | 2.04 | 1.43 | 0.50 | 0.12 | 0.02 | 0.00 | 0.00 | 0.00 | 0.00 | 0.00 | 0.00 |
| 13 | 1.21 | 0.85 | 0.30 | 0.07 | 0.01 | 0.00 | 0.00 | 0.00 | 0.00 | 0.00 | 0.00 |
| 14 | 0.66 | 0.47 | 0.16 | 0.04 | 0.00 | 0.00 | 0.00 | 0.00 | 0.00 | 0.00 | 0.00 |
| 15 | 0.34 | 0.24 | 0.08 | 0.02 | 0.00 | 0.00 | 0.00 | 0.00 | 0.00 | 0.00 | 0.00 |
| 16 | 0.16 | 0.11 | 0.04 | 0.01 | 0.00 | 0.00 | 0.00 | 0.00 | 0.00 | 0.00 | 0.00 |
| 17 | 0.07 | 0.05 | 0.02 | 0.00 | 0.00 | 0.00 | 0.00 | 0.00 | 0.00 | 0.00 | 0.00 |
| 18 | 0.03 | 0.02 | 0.01 | 0.00 | 0.00 | 0.00 | 0.00 | 0.00 | 0.00 | 0.00 | 0.00 |
| 19 | 0.01 | 0.01 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

Number

TABLE 23-continued mean sulphate ratio: 1.40
mean lipid ratio: 7.70

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 24 mean sulphate ratio: 1.40
mean lipid ratio: 7.00

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.05 | 0.03 | 0.01 | 0.00 | 0.00 | 0.00 | 0.00 | 0.00 | 0.00 | 0.00 | 0.00 |
| 1 | 0.32 | 0.22 | 0.08 | 0.02 | 0.00 | 0.00 | 0.00 | 0.00 | 0.00 | 0.00 | 0.00 |
| 2 | 1.11 | 0.78 | 0.27 | 0.06 | 0.01 | 0.00 | 0.00 | 0.00 | 0.00 | 0.00 | 0.00 |
| 3 | 2.59 | 1.81 | 0.63 | 0.15 | 0.03 | 0.00 | 0.00 | 0.00 | 0.00 | 0.00 | 0.00 |
| 4 | 4.53 | 3.17 | 1.11 | 0.26 | 0.05 | 0.01 | 0.00 | 0.00 | 0.00 | 0.00 | 0.00 |
| 5 | 6.34 | 4.44 | 1.55 | 0.36 | 0.06 | 0.01 | 0.00 | 0.00 | 0.00 | 0.00 | 0.00 |
| 6 | 7.40 | 5.18 | 1.81 | 0.42 | 0.07 | 0.01 | 0.00 | 0.00 | 0.00 | 0.00 | 0.00 |
| 7 | 7.40 | 5.18 | 1.81 | 0.42 | 0.07 | 0.01 | 0.00 | 0.00 | 0.00 | 0.00 | 0.00 |
| 8 | 6.47 | 4.53 | 1.59 | 0.37 | 0.06 | 0.01 | 0.00 | 0.00 | 0.00 | 0.00 | 0.00 |
| 9 | 5.04 | 3.52 | 1.23 | 0.29 | 0.05 | 0.01 | 0.00 | 0.00 | 0.00 | 0.00 | 0.00 |
| 10 | 3.52 | 2.47 | 0.86 | 0.20 | 0.04 | 0.00 | 0.00 | 0.00 | 0.00 | 0.00 | 0.00 |
| 11 | 2.24 | 1.57 | 0.55 | 0.13 | 0.02 | 0.00 | 0.00 | 0.00 | 0.00 | 0.00 | 0.00 |
| 12 | 1.31 | 0.92 | 0.32 | 0.07 | 0.01 | 0.00 | 0.00 | 0.00 | 0.00 | 0.00 | 0.00 |
| 13 | 0.70 | 0.49 | 0.17 | 0.04 | 0.01 | 0.00 | 0.00 | 0.00 | 0.00 | 0.00 | 0.00 |
| 14 | 0.35 | 0.25 | 0.09 | 0.02 | 0.00 | 0.00 | 0.00 | 0.00 | 0.00 | 0.00 | 0.00 |
| 15 | 0.16 | 0.12 | 0.04 | 0.01 | 0.00 | 0.00 | 0.00 | 0.00 | 0.00 | 0.00 | 0.00 |
| 16 | 0.07 | 0.05 | 0.02 | 0.00 | 0.00 | 0.00 | 0.00 | 0.00 | 0.00 | 0.00 | 0.00 |
| 17 | 0.03 | 0.02 | 0.01 | 0.00 | 0.00 | 0.00 | 0.00 | 0.00 | 0.00 | 0.00 | 0.00 |
| 18 | 0.01 | 0.01 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |

TABLE 24-continued mean sulphate ratio: 1.40
mean lipid ratio: 7.00

| | | | | | | | | | | |
|---|---|---|---|---|---|---|---|---|---|---|
| 6 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 |

TABLE 25 mean sulphate ratio: 1.40
mean lipid ratio: 3.40

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.01 | 0.01 | 0.00 | 0.00 | 0.00 | 0.00 | 0.00 | 0.00 | 0.00 | 0.00 | 0.00 |
| 1 | 0.09 | 0.07 | 0.02 | 0.01 | 0.00 | 0.00 | 0.00 | 0.00 | 0.00 | 0.00 | 0.00 |
| 2 | 0.39 | 0.28 | 0.10 | 0.02 | 0.00 | 0.00 | 0.00 | 0.00 | 0.00 | 0.00 | 0.00 |
| 3 | 1.10 | 0.77 | 0.27 | 0.06 | 0.01 | 0.00 | 0.00 | 0.00 | 0.00 | 0.00 | 0.00 |
| 4 | 2.32 | 1.62 | 0.57 | 0.13 | 0.02 | 0.00 | 0.00 | 0.00 | 0.00 | 0.00 | 0.00 |
| 5 | 3.89 | 2.72 | 0.95 | 0.22 | 0.04 | 0.01 | 0.00 | 0.00 | 0.00 | 0.00 | 0.00 |
| 6 | 5.45 | 3.81 | 1.33 | 0.31 | 0.05 | 0.01 | 0.00 | 0.00 | 0.00 | 0.00 | 0.00 |
| 7 | 6.54 | 4.58 | 1.60 | 0.37 | 0.07 | 0.01 | 0.00 | 0.00 | 0.00 | 0.00 | 0.00 |
| 8 | 6.86 | 4.81 | 1.68 | 0.39 | 0.07 | 0.01 | 0.00 | 0.00 | 0.00 | 0.00 | 0.00 |
| 9 | 6.41 | 4.49 | 1.57 | 0.37 | 0.06 | 0.01 | 0.00 | 0.00 | 0.00 | 0.00 | 0.00 |
| 10 | 5.38 | 3.77 | 1.32 | 0.31 | 0.05 | 0.01 | 0.00 | 0.00 | 0.00 | 0.00 | 0.00 |
| 11 | 4.11 | 2.88 | 1.01 | 0.23 | 0.04 | 0.00 | 0.00 | 0.00 | 0.00 | 0.00 | 0.00 |
| 12 | 2.88 | 2.01 | 0.70 | 0.16 | 0.03 | 0.00 | 0.00 | 0.00 | 0.00 | 0.00 | 0.00 |
| 13 | 1.86 | 1.30 | 0.46 | 0.11 | 0.02 | 0.00 | 0.00 | 0.00 | 0.00 | 0.00 | 0.00 |
| 14 | 1.12 | 0.78 | 0.27 | 0.06 | 0.01 | 0.00 | 0.00 | 0.00 | 0.00 | 0.00 | 0.00 |
| 15 | 0.62 | 0.44 | 0.15 | 0.04 | 0.01 | 0.00 | 0.00 | 0.00 | 0.00 | 0.00 | 0.00 |
| 16 | 0.33 | 0.23 | 0.08 | 0.02 | 0.00 | 0.00 | 0.00 | 0.00 | 0.00 | 0.00 | 0.00 |
| 17 | 0.16 | 0.11 | 0.04 | 0.01 | 0.00 | 0.00 | 0.00 | 0.00 | 0.00 | 0.00 | 0.00 |
| 18 | 0.08 | 0.05 | 0.02 | 0.00 | 0.00 | 0.00 | 0.00 | 0.00 | 0.00 | 0.00 | 0.00 |
| 19 | 0.03 | 0.02 | 0.01 | 0.00 | 0.00 | 0.00 | 0.00 | 0.00 | 0.00 | 0.00 | 0.00 |
| 20 | 0.01 | 0.01 | 0.00 | 0.00 | 0.00 | 0.00 | 0.00 | 0.00 | 0.00 | 0.00 | 0.00 |
| 21 | 0.01 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |

TABLE 25-continued mean sulphate ratio: 1.40
mean lipid ratio: 3.40

| | | | | | | | | | | | |
|---|---|---|---|---|---|---|---|---|---|---|---|
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

EXAMPLE 3

A composition of CD derivatives were produced (and the chemical compositions thereof were determined) in the same manner as described above in Example 1, but with the following exceptions: (1) N-methylpyrrolidinone was used as a solvent in place of dimethylformamide; (2) that the anhydrous N-methylpyrrolidinone/anhydrous pyridin mixture was a 5:2 (v/v) mixture of anhydrous N-methylpyrrolidinone (5 parts) and anhydrous pyridin (2 parts); (3) that respective 280 gram samples of the dried CD was solubilized in respective 2000 ml samples of the anhydrous N-methylpyrrolidinone/pyridin mixture; and (4) that the quantities of lauroylchloride and chlorosulphonic acid were altered to be those which are set forth below in Table 26:

TABLE 26

Chemical Composition of CD Derivative Solution

| Solution Designation | # of Grams of chlorosulphonic acid added | # of Grams of lauroylchloride added | Mean Sulfate Ratio[1] | Mean Lipid Ratio[2] |
|---|---|---|---|---|
| Solution # 24 | 38 | 498 | 1.33 | 8.33 |
| Solution # 25 | 38 | 476 | 1.40 | 8.61 |
| Solution # 26 | 40 | 504 | 1.33 | 8.75 |

[1]Mean sulfate ratio is expressed as the mean number of bound sulphate groups per cyclodextrin molecule.
[2]Mean lipid ratio is expressed as the mean number of bound lipid groups per cyclodextrin molecule.

The precise distribution the different CD derivatives of the present invention which are present in the respective solutions prepared by the use of the method of the present invention, as described above in this Example, were determined using the same formula as described above in Example 1, the results thereof being set forth as follows in Tables 27–29:

TABLE 26 mean sulphate ratio: 1.33
mean lipid ratio: 8.33

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.01 | 0.01 | 0.00 | 0.00 | 0.00 | 0.00 | 0.00 | 0.00 | 0.00 | 0.00 | 0.00 |
| 1 | 0.10 | 0.07 | 0.02 | 0.01 | 0.00 | 0.00 | 0.00 | 0.00 | 0.00 | 0.00 | 0.00 |
| 2 | 0.42 | 0.29 | 0.10 | 0.02 | 0.00 | 0.00 | 0.00 | 0.00 | 0.00 | 0.00 | 0.00 |
| 3 | 1.15 | 0.81 | 0.28 | 0.07 | 0.01 | 0.00 | 0.00 | 0.00 | 0.00 | 0.00 | 0.00 |
| 4 | 2.40 | 1.68 | 0.59 | 0.14 | 0.02 | 0.00 | 0.00 | 0.00 | 0.00 | 0.00 | 0.00 |
| 5 | 4.00 | 2.80 | 0.98 | 0.23 | 0.04 | 0.01 | 0.00 | 0.00 | 0.00 | 0.00 | 0.00 |
| 6 | 5.56 | 3.89 | 1.36 | 0.32 | 0.06 | 0.01 | 0.00 | 0.00 | 0.00 | 0.00 | 0.00 |
| 7 | 6.61 | 4.63 | 1.62 | 0.38 | 0.07 | 0.01 | 0.00 | 0.00 | 0.00 | 0.00 | 0.00 |
| 8 | 6.89 | 4.82 | 1.69 | 0.39 | 0.07 | 0.01 | 0.00 | 0.00 | 0.00 | 0.00 | 0.00 |
| 9 | 6.37 | 4.46 | 1.56 | 0.36 | 0.06 | 0.01 | 0.00 | 0.00 | 0.00 | 0.00 | 0.00 |
| 10 | 5.31 | 3.72 | 1.30 | 0.30 | 0.05 | 0.01 | 0.00 | 0.00 | 0.00 | 0.00 | 0.00 |
| 11 | 4.02 | 2.81 | 0.98 | 0.23 | 0.04 | 0.00 | 0.00 | 0.00 | 0.00 | 0.00 | 0.00 |
| 12 | 2.79 | 1.95 | 0.68 | 0.16 | 0.03 | 0.00 | 0.00 | 0.00 | 0.00 | 0.00 | 0.00 |
| 13 | 1.79 | 1.25 | 0.44 | 0.10 | 0.02 | 0.00 | 0.00 | 0.00 | 0.00 | 0.00 | 0.00 |
| 14 | 1.06 | 0.74 | 0.26 | 0.06 | 0.01 | 0.00 | 0.00 | 0.00 | 0.00 | 0.00 | 0.00 |
| 15 | 0.59 | 0.41 | 0.14 | 0.03 | 0.01 | 0.00 | 0.00 | 0.00 | 0.00 | 0.00 | 0.00 |
| 16 | 0.31 | 0.22 | 0.08 | 0.02 | 0.00 | 0.00 | 0.00 | 0.00 | 0.00 | 0.00 | 0.00 |
| 17 | 0.15 | 0.11 | 0.04 | 0.01 | 0.00 | 0.00 | 0.00 | 0.00 | 0.00 | 0.00 | 0.00 |
| 18 | 0.07 | 0.05 | 0.02 | 0.00 | 0.00 | 0.00 | 0.00 | 0.00 | 0.00 | 0.00 | 0.00 |
| 19 | 0.03 | 0.02 | 0.01 | 0.00 | 0.00 | 0.00 | 0.00 | 0.00 | 0.00 | 0.00 | 0.00 |
| 20 | 0.01 | 0.01 | 0.00 | 0.00 | 0.00 | 0.00 | 0.00 | 0.00 | 0.00 | 0.00 | 0.00 |
| 21 | 0.01 | 0.00 | 0.00 | 0.00 | 0.00 | 0.00 | 0.00 | 0.00 | 0.00 | 0.00 | 0.00 |

Number

TABLE 26-continued mean sulphate ratio: 1.33
mean lipid ratio: 8.33

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 28 mean sulphate ratio: 1.40
mean lipid ratio: 8.61

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.01 | 0.01 | 0.00 | 0.00 | 0.00 | 0.00 | 0.00 | 0.00 | 0.00 | 0.00 | 0.00 |
| 1 | 0.08 | 0.05 | 0.02 | 0.00 | 0.00 | 0.00 | 0.00 | 0.00 | 0.00 | 0.00 | 0.00 |
| 2 | 0.34 | 0.23 | 0.08 | 0.02 | 0.00 | 0.00 | 0.00 | 0.00 | 0.00 | 0.00 | 0.00 |
| 3 | 0.96 | 0.67 | 0.24 | 0.06 | 0.01 | 0.00 | 0.00 | 0.00 | 0.00 | 0.00 | 0.00 |
| 4 | 2.07 | 1.45 | 0.51 | 0.12 | 0.02 | 0.00 | 0.00 | 0.00 | 0.00 | 0.00 | 0.00 |
| 5 | 3.57 | 2.50 | 0.87 | 0.20 | 0.04 | 0.00 | 0.00 | 0.00 | 0.00 | 0.00 | 0.00 |
| 6 | 5.12 | 3.59 | 1.25 | 0.29 | 0.05 | 0.01 | 0.00 | 0.00 | 0.00 | 0.00 | 0.00 |
| 7 | 6.30 | 4.41 | 1.54 | 0.36 | 0.06 | 0.01 | 0.00 | 0.00 | 0.00 | 0.00 | 0.00 |
| 8 | 6.78 | 4.75 | 1.66 | 0.39 | 0.07 | 0.01 | 0.00 | 0.00 | 0.00 | 0.00 | 0.00 |
| 9 | 6.49 | 4.54 | 1.59 | 0.37 | 0.06 | 0.01 | 0.00 | 0.00 | 0.00 | 0.00 | 0.00 |
| 10 | 5.58 | 3.91 | 1.37 | 0.32 | 0.06 | 0.01 | 0.00 | 0.00 | 0.00 | 0.00 | 0.00 |
| 11 | 4.37 | 3.06 | 1.07 | 0.25 | 0.04 | 0.01 | 0.00 | 0.00 | 0.00 | 0.00 | 0.00 |
| 12 | 3.14 | 2.20 | 0.77 | 0.18 | 0.03 | 0.00 | 0.00 | 0.00 | 0.00 | 0.00 | 0.00 |
| 13 | 2.08 | 1.45 | 0.51 | 0.12 | 0.02 | 0.00 | 0.00 | 0.00 | 0.00 | 0.00 | 0.00 |
| 14 | 1.28 | 0.89 | 0.31 | 0.07 | 0.01 | 0.00 | 0.00 | 0.00 | 0.00 | 0.00 | 0.00 |
| 15 | 0.73 | 0.51 | 0.18 | 0.04 | 0.01 | 0.00 | 0.00 | 0.00 | 0.00 | 0.00 | 0.00 |
| 16 | 0.39 | 0.28 | 0.10 | 0.02 | 0.00 | 0.00 | 0.00 | 0.00 | 0.00 | 0.00 | 0.00 |
| 17 | 0.20 | 0.14 | 0.05 | 0.01 | 0.00 | 0.00 | 0.00 | 0.00 | 0.00 | 0.00 | 0.00 |
| 18 | 0.10 | 0.07 | 0.02 | 0.01 | 0.00 | 0.00 | 0.00 | 0.00 | 0.00 | 0.00 | 0.00 |
| 19 | 0.04 | 0.03 | 0.01 | 0.00 | 0.00 | 0.00 | 0.00 | 0.00 | 0.00 | 0.00 | 0.00 |
| 20 | 0.02 | 0.01 | 0.00 | 0.00 | 0.00 | 0.00 | 0.00 | 0.00 | 0.00 | 0.00 | 0.00 |
| 21 | 0.01 | 0.01 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |

TABLE 28-continued mean sulphate ratio: 1.40
mean lipid ratio: 8.61

| | | | | | | | | | | |
|---|---|---|---|---|---|---|---|---|---|---|
| 6  | 0.00 | 0.00 | 0.00 | 0.00 | 0.00 | 0.00 | 0.00 | 0.00 | 0.00 | 0.00 |
| 7  | 0.00 | 0.00 | 0.00 | 0.00 | 0.00 | 0.00 | 0.00 | 0.00 | 0.00 | 0.00 |
| 8  | 0.00 | 0.00 | 0.00 | 0.00 | 0.00 | 0.00 | 0.00 | 0.00 | 0.00 | 0.00 |
| 9  | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 |

TABLE 29 mean sulphate ratio: 1.33
mean lipid ratio: 8.75

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0  | 0.01 | 0.01 | 0.00 | 0.00 | 0.00 | 0.00 | 0.00 | 0.00 | 0.00 | 0.00 | 0.00 |
| 1  | 0.07 | 0.05 | 0.02 | 0.00 | 0.00 | 0.00 | 0.00 | 0.00 | 0.00 | 0.00 | 0.00 |
| 2  | 0.30 | 0.21 | 0.07 | 0.02 | 0.00 | 0.00 | 0.00 | 0.00 | 0.00 | 0.00 | 0.00 |
| 3  | 0.88 | 0.62 | 0.22 | 0.05 | 0.01 | 0.00 | 0.00 | 0.00 | 0.00 | 0.00 | 0.00 |
| 4  | 1.92 | 1.35 | 0.47 | 0.11 | 0.02 | 0.00 | 0.00 | 0.00 | 0.00 | 0.00 | 0.00 |
| 5  | 3.36 | 2.35 | 0.82 | 0.19 | 0.03 | 0.00 | 0.00 | 0.00 | 0.00 | 0.00 | 0.00 |
| 6  | 4.90 | 3.43 | 1.20 | 0.28 | 0.05 | 0.01 | 0.00 | 0.00 | 0.00 | 0.00 | 0.00 |
| 7  | 6.13 | 4.29 | 1.50 | 0.35 | 0.06 | 0.01 | 0.00 | 0.00 | 0.00 | 0.00 | 0.00 |
| 8  | 6.71 | 4.69 | 1.64 | 0.38 | 0.07 | 0.01 | 0.00 | 0.00 | 0.00 | 0.00 | 0.00 |
| 9  | 6.52 | 4.56 | 1.60 | 0.37 | 0.07 | 0.01 | 0.00 | 0.00 | 0.00 | 0.00 | 0.00 |
| 10 | 5.70 | 3.99 | 1.40 | 0.33 | 0.06 | 0.01 | 0.00 | 0.00 | 0.00 | 0.00 | 0.00 |
| 11 | 4.54 | 3.18 | 1.11 | 0.26 | 0.05 | 0.01 | 0.00 | 0.00 | 0.00 | 0.00 | 0.00 |
| 12 | 3.31 | 2.32 | 0.81 | 0.19 | 0.03 | 0.00 | 0.00 | 0.00 | 0.00 | 0.00 | 0.00 |
| 13 | 2.23 | 1.56 | 0.55 | 0.13 | 0.02 | 0.00 | 0.00 | 0.00 | 0.00 | 0.00 | 0.00 |
| 14 | 1.39 | 0.97 | 0.34 | 0.08 | 0.01 | 0.00 | 0.00 | 0.00 | 0.00 | 0.00 | 0.00 |
| 15 | 0.81 | 0.57 | 0.20 | 0.05 | 0.01 | 0.00 | 0.00 | 0.00 | 0.00 | 0.00 | 0.00 |
| 16 | 0.44 | 0.31 | 0.11 | 0.03 | 0.00 | 0.00 | 0.00 | 0.00 | 0.00 | 0.00 | 0.00 |
| 17 | 0.23 | 0.16 | 0.06 | 0.01 | 0.00 | 0.00 | 0.00 | 0.00 | 0.00 | 0.00 | 0.00 |
| 18 | 0.11 | 0.08 | 0.03 | 0.01 | 0.00 | 0.00 | 0.00 | 0.00 | 0.00 | 0.00 | 0.00 |
| 19 | 0.05 | 0.04 | 0.01 | 0.00 | 0.00 | 0.00 | 0.00 | 0.00 | 0.00 | 0.00 | 0.00 |
| 20 | 0.02 | 0.02 | 0.01 | 0.00 | 0.00 | 0.00 | 0.00 | 0.00 | 0.00 | 0.00 | 0.00 |
| 21 | 0.01 | 0.01 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0  | 0.00 | 0.00 | 0.00 | 0.00 | 0.00 | 0.00 | 0.00 | 0.00 | 0.00 | 0.00 | 0.00 |
| 1  | 0.00 | 0.00 | 0.00 | 0.00 | 0.00 | 0.00 | 0.00 | 0.00 | 0.00 | 0.00 | 0.00 |
| 2  | 0.00 | 0.00 | 0.00 | 0.00 | 0.00 | 0.00 | 0.00 | 0.00 | 0.00 | 0.00 | 0.00 |
| 3  | 0.00 | 0.00 | 0.00 | 0.00 | 0.00 | 0.00 | 0.00 | 0.00 | 0.00 | 0.00 | 0.00 |
| 4  | 0.00 | 0.00 | 0.00 | 0.00 | 0.00 | 0.00 | 0.00 | 0.00 | 0.00 | 0.00 | 0.00 |
| 5  | 0.00 | 0.00 | 0.00 | 0.00 | 0.00 | 0.00 | 0.00 | 0.00 | 0.00 | 0.00 | 0.00 |
| 6  | 0.00 | 0.00 | 0.00 | 0.00 | 0.00 | 0.00 | 0.00 | 0.00 | 0.00 | 0.00 | 0.00 |
| 7  | 0.00 | 0.00 | 0.00 | 0.00 | 0.00 | 0.00 | 0.00 | 0.00 | 0.00 | 0.00 | 0.00 |
| 8  | 0.00 | 0.00 | 0.00 | 0.00 | 0.00 | 0.00 | 0.00 | 0.00 | 0.00 | 0.00 | 0.00 |
| 9  | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |

TABLE 29-continued mean sulphate ratio: 1.33
mean lipid ratio: 8.75

| | | | | | | | | | | | |
|---|---|---|---|---|---|---|---|---|---|---|---|
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

EXAMPLE 4

A composition of CD derivatives were produced (and the chemical compositions thereof were determined) in the same manner as described above in Example 1, but with the following exceptions: (1) N-methylpyrrolidinone was used as a solvent in place of dimethylformamide; (2) that the anhydrous N-methylpyrrolidinone/anhydrous pyridin mixture was a 6:1 (v/v) mixture of anhydrous N-methylpyrrolidinone (6 parts) and anhydrous pyridin (1 part); (3) that respective 10 gram samples of the dried CD was solubilized in respective 35 ml samples of the anhydrous N-methylpyrrolidinone/pyridin mixture; and (4) that the quantities of lauroylchloride and chlorosulphonic acid were altered to be those which are set forth below in Table 30:

TABLE 30

Chemical Composition of CD Derivative Solution

| Solution Designation | # of Grams of chlorosulphonic acid added | # of Grams of lauroylchloride added | Mean Sulfate Ratio[1] | Mean Lipid Ratio[2] |
|---|---|---|---|---|
| Solution # 27 | 8.9 | 39.00 | 0.70 | 19.34 |
| Solution # 28 | 177 | 1.90 | 8.78 | Undetectable |

[1]Mean sulfate ratio is expressed as the mean number of bound sulphate groups per cyclodextrin molecule.
[2]Mean lipid ratio is expressed as the mean number of bound lipid groups per cyclodextrin molecule.

The precise distribution the different CD derivatives of the present invention which are present in the respective solutions prepared by the use of the method of the present invention, as described above in this Example, were determined using the same formula as described above in Example 1, the results thereof being set forth as follows in Tables 31–32:

TABLE 31 mean sulphate ratio: 0.70
mean lipid ratio: 19.34

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.01 | 0.01 | 0.00 | 0.00 | 0.00 | 0.00 | 0.00 | 0.00 | 0.00 | 0.00 | 0.00 |
| 4 | 0.03 | 0.02 | 0.01 | 0.00 | 0.00 | 0.00 | 0.00 | 0.00 | 0.00 | 0.00 | 0.00 |
| 5 | 0.07 | 0.05 | 0.02 | 0.00 | 0.00 | 0.00 | 0.00 | 0.00 | 0.00 | 0.00 | 0.00 |
| 6 | 0.16 | 0.12 | 0.04 | 0.01 | 0.00 | 0.00 | 0.00 | 0.00 | 0.00 | 0.00 | 0.00 |
| 7 | 0.35 | 0.25 | 0.09 | 0.02 | 0.00 | 0.00 | 0.00 | 0.00 | 0.00 | 0.00 | 0.00 |
| 8 | 0.70 | 0.49 | 0.17 | 0.04 | 0.01 | 0.00 | 0.00 | 0.00 | 0.00 | 0.00 | 0.00 |
| 9 | 1.31 | 0.92 | 0.32 | 0.07 | 0.01 | 0.00 | 0.00 | 0.00 | 0.00 | 0.00 | 0.00 |
| 10 | 2.24 | 1.57 | 0.55 | 0.13 | 0.02 | 0.00 | 0.00 | 0.00 | 0.00 | 0.00 | 0.00 |
| 11 | 3.52 | 2.47 | 0.86 | 0.20 | 0.04 | 0.00 | 0.00 | 0.00 | 0.00 | 0.00 | 0.00 |
| 12 | 5.04 | 3.52 | 1.23 | 0.29 | 0.05 | 0.01 | 0.00 | 0.00 | 0.00 | 0.00 | 0.00 |
| 13 | 6.47 | 4.53 | 1.59 | 0.37 | 0.06 | 0.01 | 0.00 | 0.00 | 0.00 | 0.00 | 0.00 |
| 14 | 7.40 | 5.18 | 1.81 | 0.42 | 0.07 | 0.01 | 0.00 | 0.00 | 0.00 | 0.00 | 0.00 |
| 15 | 7.40 | 5.18 | 1.81 | 0.42 | 0.07 | 0.01 | 0.00 | 0.00 | 0.00 | 0.00 | 0.00 |
| 16 | 6.34 | 4.44 | 1.55 | 0.36 | 0.06 | 0.01 | 0.00 | 0.00 | 0.00 | 0.00 | 0.00 |
| 17 | 4.53 | 3.17 | 1.11 | 0.26 | 0.05 | 0.01 | 0.00 | 0.00 | 0.00 | 0.00 | 0.00 |
| 18 | 2.59 | 1.81 | 0.63 | 0.15 | 0.03 | 0.00 | 0.00 | 0.00 | 0.00 | 0.00 | 0.00 |
| 19 | 1.11 | 0.78 | 0.27 | 0.06 | 0.01 | 0.00 | 0.00 | 0.00 | 0.00 | 0.00 | 0.00 |
| 20 | 0.32 | 0.22 | 0.08 | 0.02 | 0.00 | 0.00 | 0.00 | 0.00 | 0.00 | 0.00 | 0.00 |
| 21 | 0.05 | 0.03 | 0.01 | 0.00 | 0.00 | 0.00 | 0.00 | 0.00 | 0.00 | 0.00 | 0.00 |

TABLE 31-continued mean sulphate ratio: 0.70
mean lipid ratio: 19.34

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0  | 0.00 | 0.00 | 0.00 | 0.00 | 0.00 | 0.00 | 0.00 | 0.00 | 0.00 | 0.00 | 0.00 |
| 1  | 0.00 | 0.00 | 0.00 | 0.00 | 0.00 | 0.00 | 0.00 | 0.00 | 0.00 | 0.00 | 0.00 |
| 2  | 0.00 | 0.00 | 0.00 | 0.00 | 0.00 | 0.00 | 0.00 | 0.00 | 0.00 | 0.00 | 0.00 |
| 3  | 0.00 | 0.00 | 0.00 | 0.00 | 0.00 | 0.00 | 0.00 | 0.00 | 0.00 | 0.00 | 0.00 |
| 4  | 0.00 | 0.00 | 0.00 | 0.00 | 0.00 | 0.00 | 0.00 | 0.00 | 0.00 | 0.00 | 0.00 |
| 5  | 0.00 | 0.00 | 0.00 | 0.00 | 0.00 | 0.00 | 0.00 | 0.00 | 0.00 | 0.00 | 0.00 |
| 6  | 0.00 | 0.00 | 0.00 | 0.00 | 0.00 | 0.00 | 0.00 | 0.00 | 0.00 | 0.00 | 0.00 |
| 7  | 0.00 | 0.00 | 0.00 | 0.00 | 0.00 | 0.00 | 0.00 | 0.00 | 0.00 | 0.00 | 0.00 |
| 8  | 0.00 | 0.00 | 0.00 | 0.00 | 0.00 | 0.00 | 0.00 | 0.00 | 0.00 | 0.00 | 0.00 |
| 9  | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 32 mean sulphate ratio: 2.52
mean lipid ratio: 2.59

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0  | 49.61 | 34.73 | 12.15 | 2.84 | 0.50 | 0.07 | 0.01 | 0.00 | 0.00 | 0.00 | 0.00 |
| 1  | 0.05  | 0.03  | 0.01  | 0.00 | 0.00 | 0.00 | 0.00 | 0.00 | 0.00 | 0.00 | 0.00 |
| 2  | 0.00  | 0.00  | 0.00  | 0.00 | 0.00 | 0.00 | 0.00 | 0.00 | 0.00 | 0.00 | 0.00 |
| 3  | 0.00  | 0.00  | 0.00  | 0.00 | 0.00 | 0.00 | 0.00 | 0.00 | 0.00 | 0.00 | 0.00 |
| 4  | 0.00  | 0.00  | 0.00  | 0.00 | 0.00 | 0.00 | 0.00 | 0.00 | 0.00 | 0.00 | 0.00 |
| 5  | 0.00  | 0.00  | 0.00  | 0.00 | 0.00 | 0.00 | 0.00 | 0.00 | 0.00 | 0.00 | 0.00 |
| 6  | 0.00  | 0.00  | 0.00  | 0.00 | 0.00 | 0.00 | 0.00 | 0.00 | 0.00 | 0.00 | 0.00 |
| 7  | 0.00  | 0.00  | 0.00  | 0.00 | 0.00 | 0.00 | 0.00 | 0.00 | 0.00 | 0.00 | 0.00 |
| 8  | 0.00  | 0.00  | 0.00  | 0.00 | 0.00 | 0.00 | 0.00 | 0.00 | 0.00 | 0.00 | 0.00 |
| 9  | 0.00  | 0.00  | 0.00  | 0.00 | 0.00 | 0.00 | 0.00 | 0.00 | 0.00 | 0.00 | 0.00 |
| 10 | 0.00  | 0.00  | 0.00  | 0.00 | 0.00 | 0.00 | 0.00 | 0.00 | 0.00 | 0.00 | 0.00 |
| 11 | 0.00  | 0.00  | 0.00  | 0.00 | 0.00 | 0.00 | 0.00 | 0.00 | 0.00 | 0.00 | 0.00 |
| 12 | 0.00  | 0.00  | 0.00  | 0.00 | 0.00 | 0.00 | 0.00 | 0.00 | 0.00 | 0.00 | 0.00 |
| 13 | 0.00  | 0.00  | 0.00  | 0.00 | 0.00 | 0.00 | 0.00 | 0.00 | 0.00 | 0.00 | 0.00 |
| 14 | 0.00  | 0.00  | 0.00  | 0.00 | 0.00 | 0.00 | 0.00 | 0.00 | 0.00 | 0.00 | 0.00 |
| 15 | 0.00  | 0.00  | 0.00  | 0.00 | 0.00 | 0.00 | 0.00 | 0.00 | 0.00 | 0.00 | 0.00 |
| 16 | 0.00  | 0.00  | 0.00  | 0.00 | 0.00 | 0.00 | 0.00 | 0.00 | 0.00 | 0.00 | 0.00 |
| 17 | 0.00  | 0.00  | 0.00  | 0.00 | 0.00 | 0.00 | 0.00 | 0.00 | 0.00 | 0.00 | 0.00 |
| 18 | 0.00  | 0.00  | 0.00  | 0.00 | 0.00 | 0.00 | 0.00 | 0.00 | 0.00 | 0.00 | 0.00 |
| 19 | 0.00  | 0.00  | 0.00  | 0.00 | 0.00 | 0.00 | 0.00 | 0.00 | 0.00 | 0.00 | 0.00 |
| 20 | 0.00  | 0.00  | 0.00  | 0.00 | 0.00 | 0.00 | 0.00 | 0.00 | 0.00 | 0.00 | 0.00 |
| 21 | 0.00  | 0.00  | 0.00  | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |

TABLE 32-continued mean sulphate ratio: 2.52
mean lipid ratio: 2.59

| | | | | | | | | | | | |
|---|---|---|---|---|---|---|---|---|---|---|---|
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

EXAMPLE 5

Water was removed from 310 gram samples of β-CD (ACROS) by heating of the 310 gram samples for 4 hours at 120° C., yielding approximately 280 grams of dried CD.

Water was removed from a 5:2 (v/v) mixture of anhydrous N-methylpyrrolidinone (5 parts) and anhydrous pyridin (2 parts) by adding thereto molecular sieves (2A by MERCK, Darmstadt Germany) and incubating the mixture in a closed container for at least 48 hours at room temperature. The anhydrous N-methylpyrrolidinone/pyridin mixture was then separated from the molecular sieves by decanting the anhydrous mixture into a dry container.

Respective 280 gram samples of the dried CD was then solubilized in respective 2000 ml samples of the anhydrous N-methylpyrrolidinone/pyridin mixture.

Lauroylchloride was then added to the respective solubilized CD samples in the quantities set forth below in Table 33 and the reaction mixtures incubated for six hours at 60° C., followed by incubation for 18 hours at temperatures of between 15 and 22° C. (room temperature). In this manner, L-CD solutions are obtained.

Chlorosulphonic acid, in the quantities set forth below in Table 33, were added to respective samples of the anhydrous N-methylpyrrolidinone/pyridin mixture which was prepared as described above. These respective mixtures were then added to respective L-CD solutions, as is also set forth in Table 33. The reaction mixtures thus obtained were then incubated for 24 hours at a temperature of between 15 and 22° C. (room temperature).

Following incubation, solvents were then removed from the reaction mixtures by addition thereto of (per gram CD in the reaction mixture) both 5 grams TWEEN 80 (ICI) and 5 grams ultrapure water. Then two parts (v/v) ultrapure water was added to the respective mixtures and the mixtures subsequently ultrafiltered over an ultrafiltration membrane of regenerated cellulose with a 10 kD (kilodalton) cut-off (HOECHST) until the original volume was recovered.

The procedure of adding two parts (v/v) of ultrapure water to the recovered residue followed by ultrafiltration was then repeated twelve times to ensure that the solvent concentration was within an acceptable level.

In this manner, aqueous solutions of the CD derivatives plus TWEEN 80 in ultrapure water were obtained.

The chemical compositions of the CD derivatives obtained were then determined as described at length above in Example 1 and are herebelow summarized in Table 33:

TABLE 33

Chemical Composition of CD Derivative Solution

| Solution Designation | # of Grams of chlorosulphonic acid added | # of Grams of lauroylchloride added | Mean Sulfate Ratio[1] | Mean Lipid Ratio[2] |
|---|---|---|---|---|
| Solution # 29 | 38 | 498 | 1.05 | 7.63 |
| Solution # 30 | 38 | 476 | 0.91 | 7.91 |
| Solution # 31 | 40 | 504 | 0.91 | 8.12 |

[1]Mean sulfate ratio is expressed as the mean number of bound sulphate groups per cyclodextrin molecule.
[2]Mean lipid ratio is expressed as the mean number of bound lipid groups per cyclodextrin molecule.

The precise distribution the different CD derivatives of the present invention which are present in the respective solutions prepared by the use of the method of the present invention, as described above in this Example, were determined using the same formula as described above in Example 1, the results thereof being set forth as follows in Tables 34–36:

TABLE 34 mean sulphate ratio: 1.05
mean lipid ratio: 7.63

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.02 | 0.02 | 0.01 | 0.00 | 0.00 | 0.00 | 0.00 | 0.00 | 0.00 | 0.00 | 0.00 |
| 1 | 0.18 | 0.13 | 0.05 | 0.01 | 0.00 | 0.00 | 0.00 | 0.00 | 0.00 | 0.00 | 0.00 |
| 2 | 0.70 | 0.49 | 0.17 | 0.04 | 0.01 | 0.00 | 0.00 | 0.00 | 0.00 | 0.00 | 0.00 |
| 3 | 1.79 | 1.25 | 0.44 | 0.10 | 0.02 | 0.00 | 0.00 | 0.00 | 0.00 | 0.00 | 0.00 |
| 4 | 3.41 | 2.38 | 0.83 | 0.19 | 0.03 | 0.00 | 0.00 | 0.00 | 0.00 | 0.00 | 0.00 |
| 5 | 5.20 | 3.64 | 1.27 | 0.30 | 0.05 | 0.01 | 0.00 | 0.00 | 0.00 | 0.00 | 0.00 |
| 6 | 6.61 | 4.63 | 1.62 | 0.38 | 0.07 | 0.01 | 0.00 | 0.00 | 0.00 | 0.00 | 0.00 |
| 7 | 7.20 | 5.04 | 1.76 | 0.41 | 0.07 | 0.01 | 0.00 | 0.00 | 0.00 | 0.00 | 0.00 |
| 8 | 6.87 | 4.81 | 1.68 | 0.39 | 0.07 | 0.01 | 0.00 | 0.00 | 0.00 | 0.00 | 0.00 |
| 9 | 5.82 | 4.08 | 1.43 | 0.33 | 0.06 | 0.01 | 0.00 | 0.00 | 0.00 | 0.00 | 0.00 |
| 10 | 4.44 | 3.11 | 1.09 | 0.25 | 0.04 | 0.01 | 0.00 | 0.00 | 0.00 | 0.00 | 0.00 |
| 11 | 3.08 | 2.16 | 0.76 | 0.18 | 0.03 | 0.00 | 0.00 | 0.00 | 0.00 | 0.00 | 0.00 |
| 12 | 1.96 | 1.37 | 0.48 | 0.11 | 0.02 | 0.00 | 0.00 | 0.00 | 0.00 | 0.00 | 0.00 |
| 13 | 1.15 | 0.81 | 0.28 | 0.07 | 0.01 | 0.00 | 0.00 | 0.00 | 0.00 | 0.00 | 0.00 |
| 14 | 0.63 | 0.44 | 0.15 | 0.04 | 0.01 | 0.00 | 0.00 | 0.00 | 0.00 | 0.00 | 0.00 |
| 15 | 0.32 | 0.22 | 0.08 | 0.02 | 0.00 | 0.00 | 0.00 | 0.00 | 0.00 | 0.00 | 0.00 |
| 16 | 0.15 | 0.11 | 0.04 | 0.01 | 0.00 | 0.00 | 0.00 | 0.00 | 0.00 | 0.00 | 0.00 |
| 17 | 0.07 | 0.05 | 0.02 | 0.00 | 0.00 | 0.00 | 0.00 | 0.00 | 0.00 | 0.00 | 0.00 |
| 18 | 0.03 | 0.02 | 0.01 | 0.00 | 0.00 | 0.00 | 0.00 | 0.00 | 0.00 | 0.00 | 0.00 |
| 19 | 0.01 | 0.01 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 35 mean sulphate ratio: 0.91
mean lipid ratio: 7.91

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.02 | 0.01 | 0.00 | 0.00 | 0.00 | 0.00 | 0.00 | 0.00 | 0.00 | 0.00 | 0.00 |
| 1 | 0.14 | 0.10 | 0.04 | 0.01 | 0.00 | 0.00 | 0.00 | 0.00 | 0.00 | 0.00 | 0.00 |
| 2 | 0.57 | 0.40 | 0.14 | 0.03 | 0.01 | 0.00 | 0.00 | 0.00 | 0.00 | 0.00 | 0.00 |
| 3 | 1.50 | 1.05 | 0.37 | 0.09 | 0.02 | 0.00 | 0.00 | 0.00 | 0.00 | 0.00 | 0.00 |

TABLE 35-continued mean sulphate ratio: 0.91
mean lipid ratio: 7.91

| | | | | | | | | | | |
|---|---|---|---|---|---|---|---|---|---|---|
| 4 | 2.97 | 2.08 | 0.73 | 0.17 | 0.03 | 0.00 | 0.00 | 0.00 | 0.00 | 0.00 |
| 5 | 4.70 | 3.29 | 1.15 | 0.27 | 0.05 | 0.01 | 0.00 | 0.00 | 0.00 | 0.00 |
| 6 | 6.20 | 4.34 | 1.52 | 0.35 | 0.06 | 0.01 | 0.00 | 0.00 | 0.00 | 0.00 |
| 7 | 7.01 | 4.90 | 1.72 | 0.40 | 0.07 | 0.01 | 0.00 | 0.00 | 0.00 | 0.00 |
| 8 | 6.93 | 4.85 | 1.70 | 0.40 | 0.07 | 0.01 | 0.00 | 0.00 | 0.00 | 0.00 |
| 9 | 6.09 | 4.26 | 1.49 | 0.35 | 0.06 | 0.01 | 0.00 | 0.00 | 0.00 | 0.00 |
| 10 | 4.82 | 3.37 | 1.18 | 0.28 | 0.05 | 0.01 | 0.00 | 0.00 | 0.00 | 0.00 |
| 11 | 3.46 | 2.42 | 0.85 | 0.20 | 0.03 | 0.00 | 0.00 | 0.00 | 0.00 | 0.00 |
| 12 | 2.28 | 1.60 | 0.56 | 0.13 | 0.02 | 0.00 | 0.00 | 0.00 | 0.00 | 0.00 |
| 13 | 1.39 | 0.97 | 0.34 | 0.08 | 0.01 | 0.00 | 0.00 | 0.00 | 0.00 | 0.00 |
| 14 | 0.78 | 0.55 | 0.19 | 0.04 | 0.01 | 0.00 | 0.00 | 0.00 | 0.00 | 0.00 |
| 15 | 0.41 | 0.29 | 0.10 | 0.02 | 0.00 | 0.00 | 0.00 | 0.00 | 0.00 | 0.00 |
| 16 | 0.20 | 0.14 | 0.05 | 0.01 | 0.00 | 0.00 | 0.00 | 0.00 | 0.00 | 0.00 |
| 17 | 0.10 | 0.07 | 0.02 | 0.01 | 0.00 | 0.00 | 0.00 | 0.00 | 0.00 | 0.00 |
| 18 | 0.04 | 0.03 | 0.01 | 0.00 | 0.00 | 0.00 | 0.00 | 0.00 | 0.00 | 0.00 |
| 19 | 0.02 | 0.01 | 0.00 | 0.00 | 0.00 | 0.00 | 0.00 | 0.00 | 0.00 | 0.00 |
| 20 | 0.01 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | |
|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

TABLE 36 mean sulphate ratio: 0.91
mean lipid ratio: 8.12

| Number of lipid groups | number of sulphate groups | | | | | | | | | | |
|---|---|---|---|---|---|---|---|---|---|---|---|
| | 0 | 1 | 2 | 3 | 4 | 5 | 6 | 7 | 8 | 9 | 10 |
| 0 | 0.01 | 0.01 | 0.00 | 0.00 | 0.00 | 0.00 | 0.00 | 0.00 | 0.00 | 0.00 | 0.00 |
| 1 | 0.12 | 0.08 | 0.03 | 0.01 | 0.00 | 0.00 | 0.00 | 0.00 | 0.00 | 0.00 | 0.00 |
| 2 | 0.49 | 0.34 | 0.12 | 0.03 | 0.00 | 0.00 | 0.00 | 0.00 | 0.00 | 0.00 | 0.00 |
| 3 | 1.32 | 0.92 | 0.32 | 0.08 | 0.01 | 0.00 | 0.00 | 0.00 | 0.00 | 0.00 | 0.00 |
| 4 | 2.68 | 1.87 | 0.66 | 0.15 | 0.03 | 0.00 | 0.00 | 0.00 | 0.00 | 0.00 | 0.00 |
| 5 | 4.35 | 3.04 | 1.06 | 0.25 | 0.04 | 0.01 | 0.00 | 0.00 | 0.00 | 0.00 | 0.00 |
| 6 | 5.88 | 4.12 | 1.44 | 0.34 | 0.06 | 0.01 | 0.00 | 0.00 | 0.00 | 0.00 | 0.00 |
| 7 | 6.82 | 4.78 | 1.67 | 0.39 | 0.07 | 0.01 | 0.00 | 0.00 | 0.00 | 0.00 | 0.00 |
| 8 | 6.93 | 4.85 | 1.70 | 0.40 | 0.07 | 0.01 | 0.00 | 0.00 | 0.00 | 0.00 | 0.00 |
| 9 | 6.25 | 4.37 | 1.53 | 0.36 | 0.06 | 0.01 | 0.00 | 0.00 | 0.00 | 0.00 | 0.00 |
| 10 | 5.07 | 3.55 | 1.24 | 0.29 | 0.05 | 0.01 | 0.00 | 0.00 | 0.00 | 0.00 | 0.00 |
| 11 | 3.75 | 2.62 | 0.92 | 0.21 | 0.04 | 0.01 | 0.00 | 0.00 | 0.00 | 0.00 | 0.00 |
| 12 | 2.53 | 1.77 | 0.62 | 0.14 | 0.03 | 0.00 | 0.00 | 0.00 | 0.00 | 0.00 | 0.00 |
| 13 | 1.58 | 1.11 | 0.39 | 0.09 | 0.02 | 0.00 | 0.00 | 0.00 | 0.00 | 0.00 | 0.00 |
| 14 | 0.92 | 0.64 | 0.22 | 0.05 | 0.01 | 0.00 | 0.00 | 0.00 | 0.00 | 0.00 | 0.00 |

TABLE 36-continued mean sulphate ratio: 0.91
mean lipid ratio: 8.12

| | | | | | | | | | | | |
|---|---|---|---|---|---|---|---|---|---|---|---|
| 15 | 0.50 | 0.35 | 0.12 | 0.03 | 0.00 | 0.00 | 0.00 | 0.00 | 0.00 | 0.00 | 0.00 |
| 16 | 0.25 | 0.18 | 0.06 | 0.01 | 0.00 | 0.00 | 0.00 | 0.00 | 0.00 | 0.00 | 0.00 |
| 17 | 0.12 | 0.08 | 0.03 | 0.01 | 0.00 | 0.00 | 0.00 | 0.00 | 0.00 | 0.00 | 0.00 |
| 18 | 0.05 | 0.04 | 0.01 | 0.00 | 0.00 | 0.00 | 0.00 | 0.00 | 0.00 | 0.00 | 0.00 |
| 19 | 0.02 | 0.02 | 0.01 | 0.00 | 0.00 | 0.00 | 0.00 | 0.00 | 0.00 | 0.00 | 0.00 |
| 20 | 0.01 | 0.01 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

| Number of lipid groups | number of sulphate groups | | | | | | | | | | |
|---|---|---|---|---|---|---|---|---|---|---|---|
| | 11 | 12 | 13 | 14 | 15 | 16 | 17 | 18 | 19 | 20 | 21 |
| 0 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 | 0.00 | 0.00 | 0.00 | 0.00 |
| 12 | 0.00 | 0.00 | 0.00 | 0.00 | 0.00 | 0.00 | 0.00 | 0.00 | 0.00 | 0.00 | 0.00 |
| 13 | 0.00 | 0.00 | 0.00 | 0.00 | 0.00 | 0.00 | 0.00 | 0.00 | 0.00 | 0.00 | 0.00 |
| 14 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 16 | 0.00 | 0.00 | 0.00 | 0.00 | 0.00 | 0.00 | 0.00 | 0.00 | 0.00 | 0.00 | 0.00 |
| 17 | 0.00 | 0.00 | 0.00 | 0.00 | 0.00 | 0.00 | 0.00 | 0.00 | 0.00 | 0.00 | 0.00 |
| 18 | 0.00 | 0.00 | 0.00 | 0.00 | 0.00 | 0.00 | 0.00 | 0.00 | 0.00 | 0.00 | 0.00 |
| 19 | 0.00 | 0.00 | 0.00 | 0.00 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 | 0.00 | 0.00 | 0.00 | 0.00 |

EXAMPLE 6

A 4.5 gram sample of β-cyclodextrin (ACROS) was solubilized in a 100 ml 1:1 (v/v) mixture of anhydrous dimethylformamide (JANSSEN CHEMICA) and anhydrous pyridin (JANSSEN CHEMICA) water was then removed from the solution by adding thereto molecular sieves (2A by MERCK, Darmstadt Germany) and incubating the mixture in a closed container for at least 48 hours at room temperature. The anhydrous mixture was then separated from the molecular sieves by decanting the anhydrous mixture into a dry container.

6.6 grams of Lauroylchloride (MERCK, GERMANY) was then added to the solubilized CD sample and the reaction mixtures incubated for six hours at 60° C., followed by incubation for 18 hours at temperatures of between 15 and 22° C. (room temperature). In this manner, L-CD solutions were obtained. 0.6 grams of Chlorosulphonic acid (MERCK, GERMANY) was then added to 10 ml sample of the anhydrous dimethylformamide/pyridin mixture which was prepared as described above in Example 1. This mixture was then added to the L-CD solution. The reaction mixture thus obtained was then incubated for 24 hours at a temperature of between 15 and 22° C. (room temperature).

Following incubation, solvents were then partially removed from the reaction mixtures by evaporation at low pressure (200 millibars) for 1–2 hours at 60° C. Solvents were further removed by extensive dialysis using a membrane of regenerated cellulose with a cut-off of 10,000 daltons (SPECTRA/POR) against isotonic phosphate buffered saline (whose composition is discussed at length above in Example 1) and subsequently against ultrapure water until no solvent was detected in the filtrate. The volume ratio of dialysate (PBS or ultrapure water) and the residue used in the dialysis was maintained at >10:1 (v/v). The dialysis procedure was conducted for at least 10 days with the dialysate being replaced at least once a day. Dry products were obtained by lyophilization of the residue at room temperature, an internal pressure of less than 0.1 mbar and a cold trap of at less than −25° C.

The chemical compositions of the CD derivatives obtained were then determined by measuring the cyclodextrin content, the bound sulphate content, the total lipid content, the free lipid content and the bound lipid content (calculated by subtracting the free lipid content from the total lipid content), as described by Hilgers, et al., VACCINE 12, at pages 653–660 (1994).

The composition of the CD derivatives were expressed as the mean number of bound sulphate groups per molecule of the cyclodextrin derivatives produced and the mean number of bound lipid groups per molecule of the cyclodextrin derivatives produced. In this regard, the calculated mean number of bound lipid groups was determined to be 7.35 bound lipid groups/CD molecule and the calculated mean number of bound sulphate groups was determined to be 1.4 bound sulphate groups/CD molecule.

A 1% (w/v) solution of the SL-CD derivatives was prepared by dissolving about 1 gram of the CD derivatives obtained in a minimal volume of about 20 ml of methyl tert-butyl ether (MERCK), adding (per gram of the CD derivative added) 2 ml of the TWEEN 80 and evaporating the tertmethyl-butyl ether at an elevated temperature (about 60° C.) and reduced pressure (80 millibar) until a viscous solution of the SL-CD derivative in the TWEEN 80 has been obtained.

10 ml of water per gram of the SL-CD derivative was slowly added. Thereafter, the appropriate volumes of PBS and either squalane (ALDRICH) or soya oil or hexadecane (SIGMA) were added to respective samples. The mixture was emulsified with a microfluidizer (MICROFLUIDICS Corp., USA) until no drops of oil larger than 2 or 3 μm were visible under the microscope (magnitude 1000). The emulsions containing, per ml, 10 mg SL-CD, 20 mg TWEEN 80 and 80 mg of either squalane, soya oil or hexadecane, were then stored at 4° C. until use.

The vaccines were prepared by mixing one volume of antigen with one volume of adjuvant. The antigens were prepared such as is described in Vaccine 12, p. 653–660 and Vaccine 12, p. 661–665 (1994). Two solutions of different antigens were used: solution I which included, per ml: 10 μg of inactivated influenza virus MRC-11 (SOLVAY DUPHAR) and 1000 μg OVA (SIGMA); and solution II which included, per ml: 4.4 μg/ml of inactivated influenza virus, strain A/swine (SOLVAY DUPHAR), 4.0 μg of inactivated influenza virus, strain MRC-11 (SOLVAY DUPHAR), 2.0 μg of inactivated influenza virus, strain X-79 (SOLVAY DUPHAR) and $10^8$ $TCID_{50}$ of inactivated pseudorabies virus (SOLVAY DUPHAR).

8–10 week old NMRI female mice (CHARLES RIVER, GERMANY), each weighing about 20 grams, were immunized by injection in the foot pad with 0.025 ml of vaccine and the antibody titres were measured three weeks later The antibody titres were expressed by geometric means ($^2$log±SEM). The analysis of the antibody titres was effectuated by standardized tests using criteria for their validity as were described previously in Vaccine 12, p. 653–660 (1994).

The Student's t test was performed to analyze the statistical significance of the results and a P<0.05 was considered as significant.

The adjuvant formulations were tested in mice in two independent experiments.

The results of these experiments are summarized below in Table 37:

TABLE 37

| Adjuvant | n | $^2$log of antibody MRC 11 | | Titres against OVA | |
|---|---|---|---|---|---|
| | | Mean | SEM | Mean | SEM |
| Experiment I | | | | | |
| SL-CD/S/W | 6 | 12.9 | 1.0 | 7.2 | 0.6 |
| SL-CD/Soya oil/W | 6 | 13.6 | 1.1 | 6.0 | 0.8 |
| Control (without adjuvant) | 6 | 11.3 | 0.7 | 3.5 | 2.0 |
| Experiment II | | | | | |
| SL-CD/S/W | 6 | 13.0 | 0.6 | 8.6 | 0.8 |
| SL-CD/Soya oil/W | 6 | 11.7 | 0.5 | 6.5 | 1.0 |
| SL-CD/hexadecane/W | 6 | 12.5 | 0.6 | 8.2 | 0.6 |
| Control (without adjuvant) | 6 | 10.0 | 0.4 | 4.2 | 0.9 |

Key
n = number of specimens
SEM = mean standard deviation
SL-CD/S/W = SL-cyclodextrin derivative-in-squalane-in-water
SL-CD/Soya oil/W = SL-cyclodextrin derivative-in-soya oil-in-water All SL-CD derivative/oil/water emulsions increase the humoral response against influenza virus, strain MRC-11 and against OVA.

EXAMPLE 7

Swine specimens, 8 to 10 weeks of age have been tested for the eventual presence of antibodies against the viral antigens in questions and the specimens with detectable antibody titres have been excluded.

The SL-CD derivatives of the present invention were synthesized as described above in example 6.

A mineral oil-in-water emulsion sold under the name SUVAXYN O/W EMULSION (SOLVAY DUPHAR) was then obtained and formulations of SL-CD derivatives in an emulsion of squalane-in-water were prepared as described above in Example 6.

Vaccines containing the adjuvant formulations were also prepared as described above in Example 6.

The formulations of SL-CD derivatives-in-squalane-in-water, of mineral oil-in-water and of no adjuvant were then tested for their adjuvant effect on swine specimens having inactivated pseudorabies virus and inactivated influenza virus strains MRC-11 and A/Swine as antigens. The animals were immunized two times (week 0 and week 3) and the antibody titres measured three weeks (week 6) after the second injection.

The results of these experiments are summarized below in Table 38:

TABLE 38

| | $^2$log of anticorps Titres in 6 Weeks | | | | | |
|---|---|---|---|---|---|---|
| | PRV | | A-SWINE | | MRC-11 | |
| Adjuvant | Mean | SEM | Mean | SEM | Mean | SEM |
| Control (No Adjuvant) | 0.5 | 0.0 | <3.3 | 0.0 | <3.9 | 0.5 |
| SL-CD/S/W | 9.0 | 1.1 | 10.1 | 1.5 | >12.9 | 2.2 |
| Mineral oil-in-water | 6.5 | 0.4 | 10.7 | 1.3 | 10.7 | 0.9 |

Key
SEM = mean standard deviation
SL-CD/S/W = SL-cyclodextrin derivative-in-squalane-in-water The antibody titres against PRV (anti-PRV) were augmented by use of emulsions of SL-CD derivatives-in-squalane-in-water (SL-CD/squalane/water). The antibody titres measured were comparable to or more elevated than those obtained by the mineral oil-in-water emulsions used in commercial products. The antibody response against A/swine and against MRC-11 were also been augmented by the formulations of SL-CD-derivatives-in-squalane-in-water (SL-CD/S/W) and mineral oil-in-water.

EXAMPLE 8

Other than the adjuvant effect, other properties are important for the evaluation of a vaccine. Among others, a local reaction is an important aspect as well as a certain reaction at the site of injection being accepted in general in certain species of animals. The local toxicity has been tested in vivo following the swelling of the mouse pads after injection of the vaccine. It showed that this method is very sensitive.

The SL-CD derivatives of the present invention were synthesized as described above in Example 6.

Formulations of SL-CD derivatives in oil-in-water emulsions of squalane-in-water, of soya oil-in-water and of hexadecane-in-water were prepared as described above in Example 6.

Vaccines containing the adjuvant formulations were also prepared as described above in Example 6.

Groups of six mice were treated with 25 μl of vaccine per subcutaneous injection in the pad of the rear left foot. The vaccine included one volume of antigen solution containing 10 μg of MRC-11 and 1 mg of ovalbumine (OVA) per ml of PBS and one volume of adjuvant.

The thickness of the pads was measured one day before and at several intervals after the injection by an semi-electronic device specially developed for this purpose by the University of Utrecht (UTRECHT, Netherlands). The precision of this apparatus is about 0.02 mm.

The swelling was calculated by substracting the thickness of the pad before the treatment and the thickness of the pad after the treatment, such thickness being expressed in 0.01 mm.

The results are summarized below in Tables 39 and 40:

TABLE 39

| | Mean Swelling ($10^{-2}$ mm) Days | | | | | | | | |
|---|---|---|---|---|---|---|---|---|---|
| Adjuvant | 1 | 2 | 3 | 4 | 7 | 11 | 14 | 18 | 25 |
| Experience I | | | | | | | | | |
| SL-CD/S/W | 88 | 21 | 8 | 8 | 9 | 3 | 6 | 12 | −1 |
| SL-CD/Soya oil/W | 2 | 0 | 0 | 0 | 0 | 0 | 4 | 10 | −7 |
| Control (without adjuvant) | 2 | 0 | 0 | 0 | 0 | 0 | 4 | −6 | −4 |

SL-CD/S/W = SL-cyclodextrin derivative-in-squalane-in-water
SL-CD/Soya oil/W = SL-cyclodextrin derivative-in-soya oil-in-water

TABLE 40

| | Mean Swelling ($10^{-2}$ mm) Days | | | | | |
|---|---|---|---|---|---|---|
| Adjuvant | 1 | 2 | 6 | 10 | 17 | 22 |
| Experience II | | | | | | |
| SL-CD/S/W | 62 | 54 | 10 | 15 | 17 | 1 |
| SL-CD/Soya oil/W | 19 | 16 | 21 | 16 | 11 | 12 |
| SL-CD/hexadecane/W | 107 | 74 | 14 | 10 | 25 | 0 |
| Control (without adjuvant) | 2 | 0 | 0 | 0 | 0 | 0 |

SL-CD/S/W = SL-cyclodextrin derivative-in-squalane-in-water
SL-CD/Soya oil/W = SL-cyclodextrin derivative-in-soya oil-in-water
SL-CD/hexadecane/W = SL-cyclodextrin derivative-in-hexadecane-in-water From the above Tables, the reactogenicity of SL-CD included in the different oils has been very weak or absent. The emulsions containing SL-cyclodextrin in squalane and hexadecane provoked some swelling for one or two days after the injection, whereas the SL-cyclodextrin in soya oil did not provoke a visible response.

The reactogenicity, that is to say, the local toxicity tested on mice show pronounced effects in function of the type of oil.

EXAMPLE 9

The SL-CD derivatives of the present invention were synthesized as described above in Example 6.

Formulations of SL-CD derivatives in oil-in-water emulsions of squalane-in-water, of soya oil-in-water and of hexadecane-in-water were prepared as described above in Example 6.

The stability of the emulsions was tested in vitro by exposing the formulations to an elevated temperature during a fixed period of time. In general, emulsions are less stable at high temperatures and the test at elevated temperatures was considered as giving indications on the behavior on long term at lower temperatures.

The stability of the emulsions was determined at 37° C. Sterile aliquots of 5 ml of emulsion comprising 0.01 % (w/v) of thimersol (SIGMA), were incubated at 37° C. and the formation of oil drops, the appearance of an oil phase and other modifications have been verified each day by inspection of the emulsions with the naked eye.

The results are summarized below in Table 41:

TABLE 41

| | Stability at 37° C. Days | | | | | | | | | |
|---|---|---|---|---|---|---|---|---|---|---|
| Adjuvant | 1 | 2 | 7 | 10 | 14 | 21 | 28 | 35 | 46 | 53 | 115 |
| SL-CD/S/W | + | + | + | + | + | + | + | + | + | + | ±/+ |
| SL-CD/Soya oil/W | + | + | + | + | + | + | + | + | + | + | + |
| SL-CD/hexadecane/W | + | + | + | + | + | + | + | + | + | + | ± | key
SL-CD/S/W = SL-cyclodextrin derivative-in-squalane-in-water
SL-CD/Soya oil/W = SL-cyclodextrin derivative-in-soya oil-in-water
SL-CD/hexadecane/W = SL-cyclodextrin derivative-in-hexadecane-in-water
+ = white homogenous emulsion, no oil drops visible with naked eye
± = small drops of oil on the liquid phase visible to the naked eye
±/+ = between ± and +

The SL-CD derivatives of the present invention have a remarkable stability when incorporated into oil emulsions of squalane, soya oil and hexadecane, remaining stable for more than 53 days at 37° C.

Obviously many modifications may be made without departing from the basic spirit of the invention. Accordingly, it will be appreciated by those skilled in the art that, within the scope of the appended claims, the invention may be practiced other than has been specifically described herein.

What is claimed is:

1. An adjuvant composition comprising a cyclodextrin derivative in an oil and water emulsion, said cyclodextrin derivative substituted by at least one but no more than N−1 groups of linear hydrocarbon chains of at least eight carbon atoms wherein said groups are selected from alkylacyl and alkenyacyl, and at least one but no more than N−1 sulfate groups, wherein the total combined number of linear hydrocarbon chain groups and sulfate groups does not exceed N, and further wherein N is the number of hydroxyl groups of the cyclodextrin from which the derivative was obtained.

2. The adjuvant composition of claim 1, wherein said cyclodextrin derivative is further characterized by N being either eighteen, twenty-one or twenty-four.

3. The adjuvant composition of claim 1, wherein said cyclodextrin derivative is further characterized by having at least one but no more than thirteen sulfate groups.

4. The adjuvant composition of claim 1 wherein said cyclodextrin derivative is a lipid.

5. The adjuvant composition of claim 1 wherein the linear hydrocarbon chain group of said cyclodextrin derivative is an alkylacyl group.

6. The adjuvant composition of claim 4, wherein said cyclodextrin derivative is further characterized by the chains being linear carbon chains having a general formula of —OC(=O)—(CH$_2$)n—CH$_3$, wherein n is at least 6 and/or —OC(=O)—(CH$_2$)$_m$—CH=CH—(CH$_2$)$_m$—CH$_3$, wherein m is at least 6.

7. The adjuvant composition of claim 4, wherein said cyclodextrin derivative is further characterized by the chains being linear carbon chains having a general formula of —OC(=O)—(CH$_2$)$_n$—CH$_3$, wherein n is between 6 and 24.

8. The adjuvant composition of claim 6, wherein said cyclodextrin derivative is further characterized by the chains being linear carbon chains having the formula —OC(=O)—(CH$_2$)$_{10}$CH$_3$.

9. The adjuvant composition of claim 6, wherein said cyclodextrin derivative is further characterized by the chains being linear carbon chains having the formula —OC(=O)—(CH$_2$)$_7$—CH=CH—(CH$_2$)$_7$—CH$_3$.

10. The adjuvant composition of claim 1, wherein said cyclodextrin derivative is further characterized by the sulfate groups being —OSO$_3$R, wherein R is an atom that forms monovalent cations.

11. The adjuvant composition of claim 10, wherein said cyclodextrin derivative is further characterized in that R is at least one cation selected from the group consisting of H+, Na+, K+, Li+ and NH$_4$+.

12. The adjuvant composition of claim 1, wherein said cyclodextrin derivative is further characterized by having hydroxyl groups, wherein the total combined number of linear hydrocarbon chain groups, sulfate groups and hydroxyl groups does not exceed N, and further wherein N is the number of hydroxyl groups of the cyclodextrin from which the derivative was derived.

13. A vaccine comprising an antigen and an adjuvant composition comprising a cyclodextrin derivative in an oil and water emulsion, said cyclodextrin derivative substituted by at least one but no more than N−1 groups of linear hydrocarbon chains of at least eight carbon atoms wherein said groups are selected from alkylacyl and alkenyacyl, and at least one but no more than N−1 sulfate groups, wherein the total combined number of linear hydrocarbon chain groups and sulfate groups does not exceed N, and further wherein N is the number of hydroxyl groups of the cyclodextrin from which the derivative was obtained.

14. The vaccine of claim 13, wherein said cyclodextrin derivative is further characterized by N being either eighteen, twenty-one or twenty-four.

15. The vaccine of claim 13, wherein said cyclodextrin derivative is further characterized by having at least one but no more than thirteen sulfate groups.

16. The vaccine of claim 13, wherein said cyclodextrin derivative is a lipid.

17. The vaccine of claim 13, wherein the linear hydrocarbon chain group of said cyclodextrin derivative is an alkylacyl group.

18. The vaccine of claim 13, wherein said cyclodextrin derivative is further characterized by the chains being linear carbon chains having a general formula of —OC(=O)—(CH$_2$)n—CH$_3$, wherein n is at least 6 and/or —OC(=O)—(CH$_2$)$_m$—CH=CH—(CH$_2$)$_m$—CH$_3$, wherein m is at least 6.

19. The vaccine of claim 13, wherein said cyclodextrin derivative is further characterized by the chains being linear carbon chains having a general formula of —OC(=O)—(CH$_2$)$_n$—CH$_3$, wherein n is between 6 and 24.

20. The vaccine of claim 13, wherein said cyclodextrin derivative is further characterized by the chains being linear carbon chains having the formula —OC(=O)—(CH$_2$)$_{10}$CH$_3$.

21. The vaccine of claim 13, wherein said cyclodextrin derivative is further characterized by the chains being linear carbon chains having the formula —OC(=O)—(CH$_2$)$_7$—CH=CH—(CH$_2$)$_7$—CH$_3$.

22. The vaccine of claim 13, wherein said cyclodextrin derivative is further characterized by the sulfate groups being —OSO$_3$R, wherein R is an atom that forms monovalent cations.

23. The vaccine of claim 22, wherein said cyclodextrin derivative is further characterized in that R is at least one cation selected from the group consisting of H+, Na+, K+, Li+ and NH$_4$+.

24. The vaccine of claim 13, wherein said cyclodextrin derivative is further characterized by having hydroxyl groups, wherein the total combined number of linear hydrocarbon chain groups, sulfate groups and hydroxyl groups does not exceed N, and further wherein N is the number of hydroxyl groups of the cyclodextrin from which the derivative was derived.

* * * * *